(12) United States Patent
Terai et al.

(10) Patent No.: US 12,350,293 B2
(45) Date of Patent: Jul. 8, 2025

(54) INDUCTION METHOD FOR MACROPHAGE, ANTI-INFLAMMATORY MACROPHAGE-INDUCING AGENT, AND PHARMACEUTICAL COMPOSITION

(71) Applicant: NIIGATA UNIVERSITY, Niigata (JP)

(72) Inventors: Shuji Terai, Niigata (JP); Atsunori Tsuchiya, Niigata (JP); Suguru Takeuchi, Niigata (JP)

(73) Assignee: NIIGATA UNIVERSITY, Niigata (JP)

( * ) Notice: Subject to any disclaimer, the term of this patent is extended or adjusted under 35 U.S.C. 154(b) by 722 days.

(21) Appl. No.: 17/435,437

(22) PCT Filed: Mar. 6, 2020

(86) PCT No.: PCT/JP2020/009639
§ 371 (c)(1),
(2) Date: Sep. 1, 2021

(87) PCT Pub. No.: WO2020/184425
PCT Pub. Date: Sep. 17, 2020

(65) Prior Publication Data
US 2022/0062347 A1    Mar. 3, 2022

(30) Foreign Application Priority Data
Mar. 8, 2019 (JP) .................. 2019-042795

(51) Int. Cl.
*C12N 5/0786* (2010.01)
*A61K 35/28* (2015.01)
*A61P 1/16* (2006.01)

(52) U.S. Cl.
CPC ............... *A61K 35/28* (2013.01); *A61P 1/16* (2018.01); *C12N 5/0645* (2013.01)

(58) Field of Classification Search
CPC .................................... C12N 5/0645
See application file for complete search history.

(56) References Cited

U.S. PATENT DOCUMENTS

2018/0282698 A1    10/2018   Hematti et al.

FOREIGN PATENT DOCUMENTS

| JP | 2016-138092 | 8/2016 |
| JP | 2018-531979 | 11/2018 |
| KR | 10-2019-0083933 | 7/2019 |
| WO | WO2015/076717 A2 | 5/2015 |

(Continued)

OTHER PUBLICATIONS

Machine translation of Bing Huang et al., CN CN 107245472 A, 2017.*

(Continued)

*Primary Examiner* — Rosanne Kosson
(74) *Attorney, Agent, or Firm* — Barnes & Thornburg LLP

(57) ABSTRACT

An induction method for a macrophage is provided, in which macrophages are cultured in the presence of exosomes produced from a mesenchymal stem cell to which interferon gamma has been added and are induced into anti-inflammatory macrophages. An anti-inflammatory macrophage-inducing agent includes exosomes produced from a mesenchymal stem cell to which interferon gamma has been added, as an active component. A pharmaceutical composition contains the inducing agent.

8 Claims, 22 Drawing Sheets

(56) References Cited

FOREIGN PATENT DOCUMENTS

| WO | WO2017/204639 A1 | 11/2017 |
| WO | WO2018/081514 A1 | 5/2018 |

OTHER PUBLICATIONS

Lina Huang et al., Exosomes in mesenchymal stem cells, a new therapeutic strategy for cardiovascular diseases? Int J Biol Sci 11:238-245, 2015.*

Sugimoto et al., "Annexin A1 and the resolution of inflammation: modulation of neutrophil recruitment, apoptosis and clearance," J Immunol Res, article ID No. 8239258, 13 pp., 2016.*

Damazo et al., "Endogenous annexin A1 counter-regulates bleomycin-induced lung fibrosis," BMC Immunol 12(59):1-13, 2011.*

Neymeyer et al., "Regulation of Annexin A1 expression in renal interstitial fibroblasts during chronic kidney disease," FASEB J vol. 26, meeting abstract, Apr. 2012.*

Rackham et al., "Annexin A1 is a key modulator of mesenchymal stromal cell-mediated improvements in islet function," Diabetes 65 : 129-139, 2016.*

Sivanathan et al., "Interferon-gamma modification of mesenchymal stem cells: implications of autologous and allogenic mesenchymal stem cell therapy in allotransplantation," Stem Cell Rev and Rep 10:351-375, 2014.*

PCT Search Report and Written Opinion prepared for PCT/JP2020/009639, mailed Jun. 2, 2020.

Y. Watanabe et al., "Mesenchymal Stem Cells and Induced Bone Marrow-Derived Macrophages Synergistically Improve Liver Fibrosis in Mice," 2018, Stem Cells Translational Medicine.

T. Takeuchi et al., "IFN-Gamma-Stimulated Exosomes Induce Anti-Inflammatory Macrophages and Contributes to the Improvement of Liver Fibrosis," 2019 Liver P-117, Acta Hepatologica Japonica, vol. 60, suppl. (2), A681, 2019.

* cited by examiner

INDUCTION METHOD FOR MACROPHAGE, ANTI-INFLAMMATORY MACROPHAGE-INDUCING AGENT, AND PHARMACEUTICAL COMPOSITION

CROSS-REFERENCE TO RELATED APPLICATIONS

This application is a national stage entry under 35 U.S.C. § 371(b) of PCT International Application No. PCT/JP2020/009639, filed Mar. 6, 2020, which claims the benefit of Japanese Patent Application Serial No. 2019-042795, filed Mar. 8, 2019. The disclosure of both applications is incorporated herein by reference in their entirety.

TECHNICAL FIELD

The present invention relates to an induction method for a macrophage, an anti-inflammatory macrophage-inducing agent, and a pharmaceutical composition. Priority is claimed on Japanese Patent Application No. 2019-042795, filed Mar. 8, 2019, the content of which is incorporated herein by reference.

BACKGROUND ART

A mesenchymal stem cell (MSC) can be collected not only from bone marrow but also from medical waste such as adipose tissue and umbilical cord tissue. Due to the low antigenicity of MSC, even an allogeneic cell can be used, and MSC plays various roles in anti-inflammation, anti-fibrosis, angiogenesis, antioxidation, and the like. For this reason, MSCs have been attracting a great deal of attention as a new tool in regenerative medicine, with a view to industrialization. However, it has been reported that MSCs differ slightly depending on the cell type from which they are derived and that the culture conditions or properties thereof in a case of being introduced into a living body change, and the mechanism by which their effects are exhibited has been largely unelucidated so far. MSCs are expected to act and exhibit effects on many immune cells through the production of cytokines, chemokines, growth factors, exosomes, and the like as a "conducting cell"; however, attention has been particularly paid to macrophages in the pathophysiology of liver cirrhosis.

So far, the inventors of the present invention have revealed that MSCs act on the amelioration of fibrosis and the promotion of regeneration during the progression of liver cirrhosis by changing the polarity of bone marrow-derived cultured macrophages to anti-inflammatory macrophages (also referred to as an "M2 macrophage") (see, for example, Non-Patent Document 1).

However, it is known that most MSCs are delivered to the lung in the case of being administered intravenously and that a very small population of MSCs is delivered to the liver. Nevertheless, the above effects are exhibited during the progression of liver cirrhosis, and thus it is presumed that some factors expressed by MSCs are involved; however, it has not been revealed what factors change the polarity of macrophages or what the detailed mechanism thereof is.

PRIOR ART LITERATURE

Non-Patent Document

Non-Patent Document 1: Watanabe Y et al., "Mesenchymal Stem Cells and Induced Bone Marrow-Derived Macrophages Synergistically Improve Liver Fibrosis in Mice.", Stem Cells Transl Med., 2018, doi: 10.1002/sctm.18-0105.

DISCLOSURE OF INVENTION

Problems to be Solved by the Invention

The present invention has been made in consideration of the above circumstances and provides a novel induction method for a macrophage, an anti-inflammatory macrophage-inducing agent, and a pharmaceutical composition containing the inducing agent.

Means for Solving the Problems

As a result of diligent research to achieve the above object, the inventors of the present invention focused on the fact that MSC changes expressed factors in response to various environmental changes such as inflammatory stimulation, have found that exosomes, which are produced from MSC cultured with the addition of interferon gamma (IFN-γ) among the inflammatory cytokines, change the polarity of the macrophage to induce anti-inflammatory macrophages, and have completed the present invention.

That is, the present invention includes the following aspects.

The induction method for a macrophage according to the first aspect of the present invention is a method including culturing a macrophage in the presence of exosomes produced from a mesenchymal stem cell to which interferon gamma has been added, to induce the macrophage into an anti-inflammatory macrophage.

The anti-inflammatory macrophage-inducing agent according to the second aspect of the present invention contains exosomes produced from a mesenchymal stem cell to which interferon gamma has been added, as an active component.

The pharmaceutical composition according to the third aspect of the present invention contains the inducing agent according to the second aspect.

The pharmaceutical composition according to the third aspect may be for anti-inflammatory use.

The pharmaceutical composition according to the third aspect may be for anti-fibrotic use.

The pharmaceutical composition according to the third aspect may be used for treating or preventing hepatitis or liver cirrhosis.

Effects of the Invention

According to the induction method for a macrophage and the anti-inflammatory macrophage-inducing agent according to the above aspects, it is possible to obtain an anti-inflammatory macrophage. According to the pharmaceutical composition of the above aspect, it is possible to treat or prevent a disease associated with inflammation or fibrosis.

EMBODIMENTS FOR CARRYING OUT THE INVENTION

<Macrophage>

Figure 1:
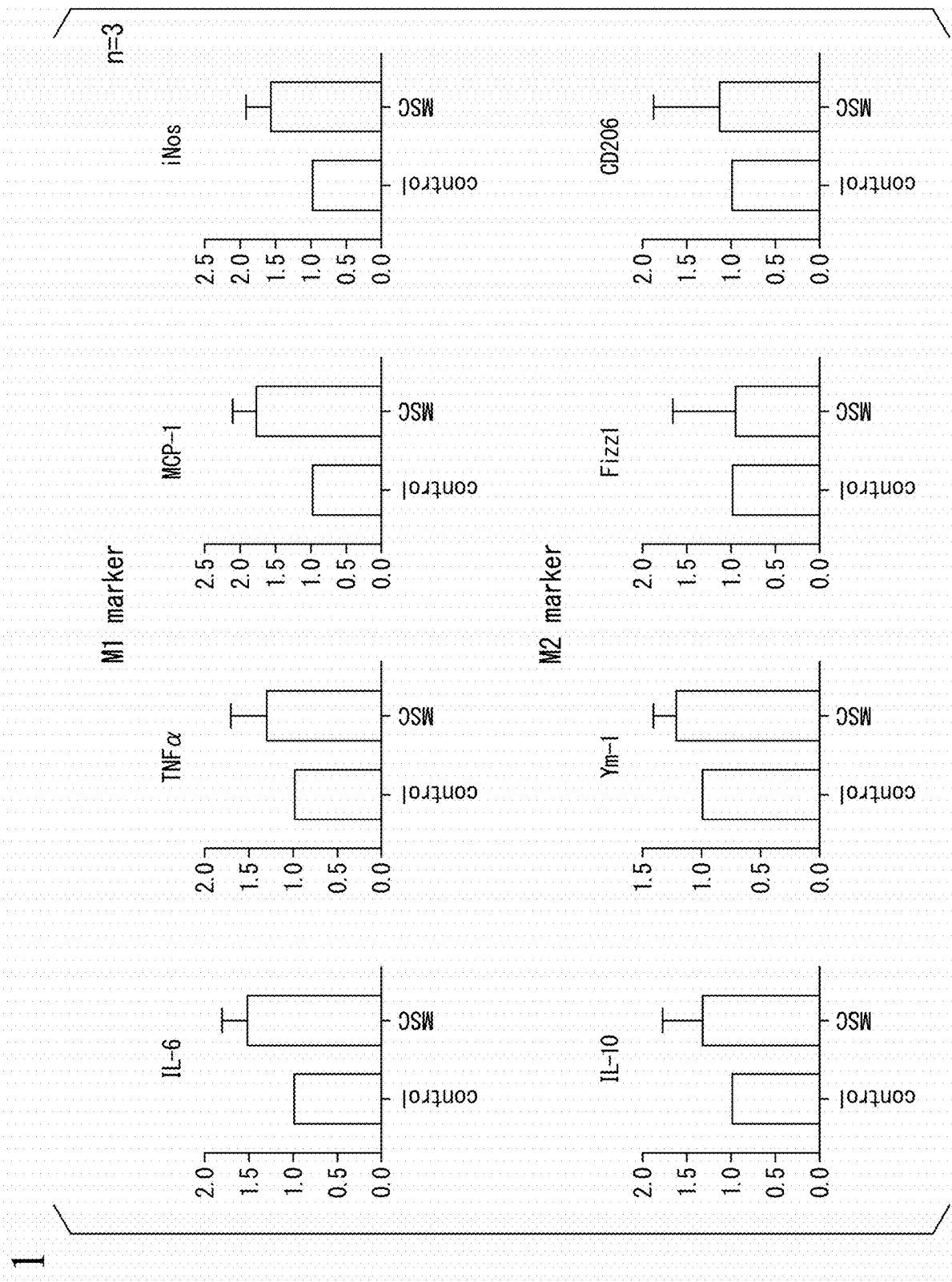
FIG. 1 is a graph showing expression levels of M1 macrophage- and M2 macrophage-specific markers in Reference Example 2.

Macrophages are roughly classified into an inflammatory macrophage (also referred to as an "M1 type" or an "M1 macrophage") and an anti-inflammatory macrophage (also referred to as an "M2 type" or an "M2 macrophage"). In general, it is conceived that an inflammatory monocyte differentiates into M1 macrophage in response to inflammatory cytokines such as tumor necrosis factor α (TNF-α) and IFN-γ and that the M1 macrophage acts protectively against infections of pathogens and parasites and is involved in fibrosis during the progression of tissue inflammation. On the other hand, it is conceived that a tissue-resident monocyte differentiates to M2 macrophage in response to Th2-type cytokines such as interleukin-4 (IL-4) and IL-13 and that the M2 macrophage is involved in tissue repair and the like and is involved in the amelioration of fibrosis during tissue curing.

Whether the polarity of the macrophage is an M1 macrophage type or an M2 macrophage type can be determined by measuring the expression levels of an M1-type-specific gene marker and an M2-type-specific gene marker. For example, in a case where the expression of an M1-type-specific gene marker is hardly detected and the expression of an M2-type-specific gene marker is detected, it can be determined that the macrophage is an M2 macrophage.

Examples of the M1-type-specific gene marker include IL-6, TNFα, monocyte chemotactic protein-1 (MCP-1), inducible nitric oxide synthase (iNos), and CD40. Examples of the M2-type-specific gene marker include IL-10, chitinase 3-like 3 (Ym-1), found in inflammatory zone 1 (Fizz1), and CD206. In addition, the expression of each gene marker can be detected by using a known method such as the PCR method or the RT-PCR method.

<Induction Method for Macrophage>

An induction method for a macrophage (hereinafter, may be abbreviated as the "induction method of the present embodiment") according to one embodiment (hereinafter, referred to as the "present embodiment") of the present invention is a method of culturing a macrophage in the presence of exosomes produced from MSC to which IFN-γ has been added, to induce the macrophage into an anti-inflammatory macrophage.

The inventors of the present invention focused on factors expressed by MSC since the factors could change the polarity of the macrophage to induce M2 macrophages and exhibit effects of amelioration of fibrosis and tissue repair, although the proportion of MSC delivered to the liver was very low in a case where MSC was intravenously administered to a living body. In addition, the inventors of the present invention have found for the first time that in a case where exosomes recovered from MSC cultured under stimulation with various inflammatory cytokines are added to macrophages, due to the fact that MSC changes expressed factors in response to various environmental changes such as inflammatory stimulation, the macrophages cultured with the addition of exosomes recovered from MSC cultured under the stimulation with IFN-γ change the polarity thereof to an anti-inflammatory macrophage type.

Since the induction method of the present embodiment has the above-described configuration, it is possible to easily obtain an anti-inflammatory macrophage.

[Exosome]

In general, an "exosome" is a membrane vesicle that is secreted from various cells, having a diameter of 40 nm or more and 150 nm or less. Nucleic acids such as miRNA and mRNA, proteins, and lipids are contained in the membrane vesicle, which is conceived to act as a signal transducing factor between cells.

The exosomes that are used in the induction method of the present embodiment are obtained from MSC cultured under stimulation with IFN-γ. Specifically, MSC is cultured in a medium containing IFN-γ for a predetermined period of 10 hours or more and 48 hours or less under typical cell culture conditions such as 37° C. and a 5% $CO_2$ concentration, and then the culture supernatant thereof is recovered to obtain exosomes.

The content of IFN-γ in the medium may be a concentration such that the exosomes produced by MSC can exhibit an ability to induce an anti-inflammatory macrophage, and for example can be 1 ng/mL or more and 500 ng/mL or less, is preferably 10 ng/mL or more and 400 ng/mL or less, more preferably 30 ng/mL or more and 300 ng/mL or less, and still more preferably 50 ng/mL or more and 200 ng/mL or less.

The medium that is used for culturing MSC is typically a serum-free medium, and a commercially available medium can be appropriately used. Examples of the commercially available medium include a mesenchymal stem cell growth medium 2 (MesenCult (registered trade name) Basal Medium (Ready-to-use)) (product code: 05514) manufactured by STEMCELL Technologies and a mesenchymal stem cell growth medium Stem Pro (registered trade name) MSC SFM (Ready-to-use) (product code: A-13829-01) manufactured by Thermo Fisher Scientific, Inc.

MSC is not particularly limited, and MSC contained in bone marrow, fat, umbilical cord, peripheral blood, dental pulp, or amnion can be used. Animal species from which MSC is derived include, but are not limited to, a human, a monkey, a dog, a cow, a horse, a sheep, a pig, a rabbit, a mouse, a rat, a guinea pig, and a hamster. Among them, a mammal is preferable, and a human is particularly preferable.

The obtained exosome may be used as it is in a state of being contained in the culture supernatant of MSC; however, it is preferable to use exosomes that are recovered, concentrated, purified, and isolated from the culture supernatant since the culture supernatant also contains other factors produced from MSC. The recovery, concentration, purification, and isolation methods are not particularly limited, and examples thereof include an ultracentrifugation method, a centrifugal sedimentation method, and a method using an antibody. The centrifugal sedimentation method is a method using low-speed centrifugation, and thus there is a risk that proteinaceous factors such as cytokines and chemokines having properties similar to exosomes may be mixed. In addition, in the recovery method using an antibody, it is difficult to remove the antibody bound to the exosome. For these reasons, it is preferable to use the ultracentrifugation method. The ultracentrifugation method includes a pellet down method, a sucrose cushion method, a density gradient centrifugation method, and the like, and the degree of purification of the exosome increases in the order of the pellet down method, the sucrose cushion method, and the density gradient centrifugation method. It is possible to appropriately select which ultracentrifugation method is used, depending on the intended purpose.

In addition, the exosome used in the induction method of the present embodiment preferably contains one or more proteins selected from the group consisting of Annexin A1, Lactadherin, Lactotransferrin, Galectin-3 binding protein, and Aminopeptidase N. As shown in Examples described later, in a case where a macrophage is cultured with the addition of each of the above five kinds of proteins, the polarity of the macrophage can be changed.

The amino acid sequence of the human Annexin A1 is disclosed, for example, as Genbank accession number NP_000691.

The amino acid sequence of human Lactadherin is disclosed, for example, as Genbank accession numbers NP_001108086.1, NP_001297248.1, NP_001297249.1, NP_001297250.1, and NP_005919.2.

The amino acid sequence of human Lactotransferrin is disclosed, for example, as Genbank accession numbers NP_001186078.1, NP_001308050.1, NP_001308051.1, and NP_002334.2.

The amino acid sequence of human Galectin-3 binding protein is disclosed, for example, as Genbank accession number NP_005558.1.

The amino acid sequence of human Aminopeptidase N is disclosed, for example, as Genbank accession numbers NP_001141.2, XP_005254949.1, and XP_011519775.1.

[Macrophage]

The macrophage that is used in the induction method of the present embodiment is not particularly limited, and may be a macrophage differentiated from a progenitor cell derived from the yolk sac or the fetal liver, or may be a macrophage differentiated from a monocyte derived from bone marrow. The animal species from which the macrophage is derived is not particularly limited, and examples thereof include the same animal species as those exemplified in MSC.

For example, in a case where macrophages are cultured in a medium containing the above exosomes for a predetermined period of about 10 hours or more and 48 hours or less under typical cell culture conditions such as 37° C. and a 5% $CO_2$ concentration, it is possible to change the polarity of the macrophage to induce anti-inflammatory macrophages.

The amount of exosomes that are used for culturing macrophages may be an amount with which an ability to induce anti-inflammatory macrophages can be exhibited. For example, the concentration of exosomes in the medium can be 1 ng/mL or more and 1 μg/mL or less, is preferably 10 ng/mL or more and 500 ng/mL or less, more preferably 20 ng/mL or more and 400 ng/mL or less, still more preferably 30 ng/mL or more and 300 ng/mL or less, and particularly preferably 40 ng/nL or more and 200 ng/mL or less, with respect to the number of macrophage cells of $5 \times 10^6$ cells.

The medium that is used for culturing macrophages may be a basal medium containing components (inorganic salts, carbohydrates, hormones, essential amino acids, non-essential amino acids, vitamins) necessary for cell survival and growth, and the like, and can be appropriately selected depending on the cell type. Examples thereof include, but are not limited to, Dulbecco's Modified Eagle's Medium (DMEM), Minimum Essential Medium (MEM), RPMI-1640, Basal Medium Eagle (BME), Dulbecco's Modified Eagle's Medium: Nutrient Mixture F-12 (DMEM/F-12), and Glasgow Minimum Essential Medium (Glasgow MEM).

The induction to anti-inflammatory macrophages, that is, the confirmation of the polarity change from an M1 type to an M2 type, can be checked by detecting an M1-type-specific gene marker and an M2-type-specific gene marker of the macrophages cultured in the presence or absence of exosomes, as shown in Examples described later. Specifically, for example, in macrophages cultured in the presence of exosomes, in a case where the expression level of the M1-type-specific gene marker is low and the expression level of the M2-type-specific gene marker is increased as compared with macrophages cultured in the absence of exosomes, it can be determined that the polarity of the macrophage is shifted from an M1 type to an M2 type.

In addition, the M2 macrophage can be isolated by performing FACS analysis on the cultured macrophages using an antibody to an M2-type-specific cell surface marker (for example, CD206).

Further, for example, in a case where the above exosomes are directly administered to a tissue containing macrophages or to the inside of a living body, it is possible to change the polarity of the macrophage to induce M2 macrophages.

<Inducing Agent and Pharmaceutical Composition>

According to the induction method of the present embodiment, as described above, the polarity of the macrophage can be easily shifted from the M1 type to the M2 type since exosomes produced from MSC to which IFN-γ has been added are used. That is, exosomes produced from MSC to which IFN-γ has been added can be said to be an anti-inflammatory macrophage-inducing agent.

An anti-inflammatory macrophage-inducing agent of the present embodiment (hereinafter, may be abbreviated as an "inducing agent of the present embodiment") may be administered alone to a living body. Alternatively, since the inducing agent of the present embodiment exhibits the effects of suppressing the inflammatory reaction and ameliorating fibrosis by changing the polarity of the macrophage to induce anti-inflammatory macrophages in a living body, the inducing agent may be mixed with a pharmaceutically acceptable carrier and administered as a pharmaceutical composition for treating or preventing a disease associated with inflammation or fibrosis. That is, the pharmaceutical composition can be said to be a pharmaceutical composition for anti-inflammatory use or anti-fibrotic use.

Examples of the disease associated with inflammation or fibrosis are not particularly limited; however, examples thereof include pneumonia, pulmonary fibrosis, hepatitis, liver cirrhosis, pancreatitis, nephritis, renal fibrosis, cystic fibrosis, enteritis, and intestinal fibrosis. Among them, the inducing agent or pharmaceutical composition of the present embodiment is preferably used for treating or preventing hepatitis or liver cirrhosis.

The pharmaceutical composition may have a dosage form to be used orally or may have a dosage form to be used parenterally; however, a dosage form to be used parenterally is preferable. Examples of the dosage forms to be used orally include a tablet, a capsule, an elixir, and a microcapsule. Examples of the dosage forms to be used parenterally include an injection agent, an inhalant, a suppository, and a patch.

As the pharmaceutically acceptable carrier, a carrier that is used for the pharmaceutical preparation of a general pharmaceutical composition can be used without particular limitation. More specific examples thereof include binders such as gelatin, cornstarch, gum tragacanth, and gum arabic; excipients such as starch and crystalline cellulose; swelling agents such as alginic acid; and solvents for an injection agent such as water, ethanol, and glycerin.

The pharmaceutical composition may contain an additive. Examples of the additive include lubricants such as calcium stearate and magnesium stearate; sweetening agents such as sucrose, lactose, saccharin, and maltitol; flavoring agents such as peppermint and Akamono (Japanese azalea) oil; stabilizers such as benzyl alcohol and phenol; buffers such as a phosphoric acid salt and sodium acetate; dissolution auxiliary agents such as benzyl benzoate and benzyl alcohol; antioxidants; and preservatives.

The pharmaceutical composition can be formulated by appropriately combining the above inducing agent with the above pharmaceutically acceptable carrier and additive and mixing them in a generally accepted unit dose form required for pharmaceutical practice.

The pharmaceutical composition may be used in combination with at least one selected from the group consisting of a therapeutic agent other than the above-described inducing agent, which has an anti-inflammatory action or an anti-fibrotic action, and a therapeutic agent for another disease. The above inducing agent and other agent may be made as the same pharmaceutical preparation or may be made as separate pharmaceutical preparations. In addition, each pharmaceutical preparation may be administered through the same route of administration or may be administered through different routes of administration. Further, each pharmaceutical preparation may be administered simultaneously, administered sequentially, or administered separately after an interval of a predetermined number of hours or a predetermined period. In one embodiment, the inducing agent and other agent may be made as a kit containing them.

Examples of the target to which the pharmaceutical composition is administered include, but are not limited to, a human, a monkey, a dog, a cow, a horse, a sheep, a pig, a rabbit, a mouse, a rat, a guinea pig, a hamster, and cells thereof. Among them, a mammal or a mammalian cell is preferable, and a human or a human cell is particularly preferable.

The administration to a human patient or an animal patient can be carried out by, for example, intrathecal injection, intraperitoneal injection, intraarterial injection, intravenous injection, or subcutaneous injection, and also can be carried out intranasally, transbronchially, intramuscularly, transcutaneously, or orally by a method known to those skilled in the art.

The dose of the pharmaceutical composition varies depending on the symptoms, body weight, age, gender, and the like of a human patient or an animal patient and thus cannot be unconditionally determined; however, in a case of oral administration, for example, the active component (the above exosome) of 0.1 mg/kg body weight or more and 100 mg/kg body weight or less per administration unit form may be administered. In a case of an injection agent, for example, the active component (the exosome) of 0.01 mg or more and 50 mg or less per administration unit form may be administered.

In addition, the daily dose of the pharmaceutical composition varies depending on the symptoms, body weight, age, gender, and the like of a human patient or an animal patient and thus cannot be unconditionally determined; however, for example, the active component of 0.1 mg/kg body weight or more and 100 mg/kg body weight or less per day for an adult may be administered once a day or administered dividedly twice or more and 4 times or less a day.

OTHER EMBODIMENTS

In one embodiment, the present invention provides a treatment method or prevention method for a disease associated with inflammation or fibrosis, in which an effective amount of the exosomes produced from the above-described MSC to which IFN-γ has been added is administered to a human patient or an animal patient in need of treatment. The above exosome preferably contains one or more proteins selected from the group consisting of Annexin A1, Lactadherin, Lactotransferrin, Galectin-3 binding protein, and Aminopeptidase N.

In one embodiment, the present invention provides exosomes that are produced from the MSC to which IFN-γ has been added and are for the treatment or prevention of a disease associated with inflammation or fibrosis.

In one embodiment, exosomes produced from the MSC to which IFN-γ has been added are used for producing a pharmaceutical composition for the treatment or prevention of a disease associated with inflammation or fibrosis.

Examples of the disease associated with inflammation or fibrosis include the same diseases as those exemplified in the above-described pharmaceutical composition, and among them, hepatitis or liver cirrhosis is preferable.

In one embodiment, the present invention provides a treatment method or prevention method for a disease associated with inflammation or fibrosis, in which an effective amount of one or more proteins selected from the group consisting of Annexin A1, Lactadherin, Lactotransferrin, Galectin-3 binding protein, and Aminopeptidase N is administered to a human patient or an animal patient in need of treatment. The "effective amount of a protein" referred to here means an amount with which the polarity of the macrophage can be changed to induce M2 macrophages.

In one embodiment, the present invention provides one or more proteins selected from the group consisting of Annexin A1, Lactadherin, Lactotransferrin, Galectin-3 binding protein, and Aminopeptidase N, and are for the treatment or prevention of a disease associated with inflammation or fibrosis.

In one embodiment, one or more proteins selected from the group consisting of Annexin A1, Lactadherin, Lactotransferrin, Galectin-3 binding protein, and Aminopeptidase N are used for producing a pharmaceutical composition for the treatment or prevention of a disease associated with inflammation or fibrosis.

Examples of the disease associated with inflammation or fibrosis include the same diseases as those exemplified in the above-described pharmaceutical composition, and among them, hepatitis or liver cirrhosis is preferable.

In one embodiment, a composition for cell culture is provided containing the above inducing agent. In a case where macrophages are cultured in the medium containing exosomes (the composition for cell culture) produced from MSC to which IFN-γ has been added, the polarity of the macrophage can be changed to induce M2 macrophages.

As shown in Examples described later, in a case where a macrophage is cultured with the addition of each of the above five kinds of proteins, the polarity of the macrophage can be changed. For this reason, instead of the exosomes produced from the above-described MSC to which IFN-γ has been added, the composition for cell culture may be prepared by using one or more proteins selected from the group consisting of Annexin A1, Lactadherin, Lactotransferrin, Galectin-3 binding protein, and Aminopeptidase N.

That is, in one embodiment, a composition for cell culture is provided containing one or more proteins selected from the group consisting of Annexin A1, Lactadherin, Lactotransferrin, Galectin-3 binding protein, and Aminopeptidase N.

The composition for cell culture may consist only of the above exosomes or may be a composition in which the above exosomes and a known diluent are mixed.

Examples of the diluent include water, a buffer, and various media.

The concentration of the exosomes in the composition for cell culture may be an amount with which an ability to induce anti-inflammatory macrophages can be exhibited. For example, the concentration thereof in the medium can be 1 ng/mL or more and 1 g/mL or less, is preferably 10 ng/mL or more and 500 ng/mL or less, more preferably 20 ng/mL or more and 400 ng/mL or less, still more preferably 30 ng/mL or more and 300 ng/mL or less, and particularly preferably 40 ng/mL or more and 200 ng/mL or less, with respect to the number of macrophage cells of $5 \times 10^6$ cells.

In addition, in the composition for cell culture, the concentration of one or more proteins selected from the group consisting of Annexin AL, Lactadherin, Lactotransferrin, Galectin-3 binding protein, and Aminopeptidase N is not particularly limited, and may be a concentration such that the polarity of the macrophage can be changed to induce M2 macrophages.

EXAMPLES

The present invention will be described with reference to Examples; however, the present invention is not limited to Examples below.

Reference Example 1

(Effect of miRNA in Exosomes Derived from Mesenchymal Stem Cell on Polarity Change of Macrophage)

miR125b and miR21 among miRNAs in exosomes derived from a human MSC, which were miRNAs highly expressed in MSCs as a whole, were examined to identify a factor that affects the polarity change of macrophage among the factors expressed by the mesenchymal stem cell (MSC).

Then, using VIROMER BLUE (registered trade name) or lipofectamine, miR125b (10 μM) and miR21 (10 μM) were introduced alone or in combination (each miRNA of 5 μM, a total of 10 μM) into macrophages ($5 \times 10^6$ cells/well) on a 6-well non-adhesive plate and cultured for 24 hours or 48 hours. After culturing for 24 hours or 48 hours, cells were harvested and the expression levels of the M1 macrophage markers IL-6, TNFα, MCP-1, iNos, and the M2 macrophage markers IL-10, Ym-1, Fizz1, and CD206 were checked by RT-PCR.

As a result of comparing a cell group in which miRNA was introduced and a cell group in which miRNA was not introduced, no change was observed in the expression levels of the M1 macrophage markers and the M2 macrophage markers (not shown in the drawing).

Reference Example 2

(Effect of Exosomes Derived from a Normally Cultured Mouse MSC on Polarity Change of Macrophage)

Next, the induction of macrophages was attempted using an in vitro system using exosomes derived from mouse MSC.

1. Recovery of Exosomes Derived from MSC

MSC was seeded in 6-well dishes and cultured in a serum-free medium. After the confluency reached about 80% of the bottom area of each well, 2 mL of the culture supernatant was recovered. Next, the recovered culture supernatant was ultracentrifuged (ultracentrifuge: Optima XL-100K, swing rotor: SW41Ti, 27,000 rpm, 110 minutes) to remove the supernatant. Then, washing with PBS was carried out, and ultracentrifugation was carried out again (the same upper limits of the rotation conditions as above) to remove the supernatant, whereby 200 μL of an exosome-containing solution was obtained. The exosome content of the obtained exosome-containing solution was checked by measuring the protein concentration using a Qubit 3.0 Fluorometer.

2. Induction of Macrophage

Next, macrophages ($5 \times 10^6$ cells/well) were cultured on a 6-well non-adhesive plate using a medium containing 1 g of the obtained exosomes. Cells were harvested 48 hours after the start of culture, and the expression levels of the M1 macrophage markers IL-6, TNFα, MCP-1, iNos, and the M2 macrophage markers IL-10, Ym-1, Fizz1, and CD206 were checked by RT-PCR. Each of the primers used for RT-PCR was purchased from QIAGEN. The product number of each primer used is as shown below.

IL-6: QIAGEN QuantiTect (registered trade name, omitted hereinafter) Primer Assay QT0098875
  TNFα: QIAGEN QuantiTect Primer Assay QT00104006
  MCP-1: QIAGEN QuantiTect Primer Assay QT009887
  iNos: QIAGEN QuantiTect Primer Assay QT001547980
  IL-10: QIAGEN QuantiTect Primer Assay QT00106169
  Ym-1: QIAGEN QuantiTect Primer Assay QT00108829
  Fizz1: QIAGEN QuantiTect Primer Assay QT00254359
  CD206: QIAGEN QuantiTect Primer Assay QT00103012

The measurement results are shown in FIG. 1. In FIG. 1, "Control" is a cell group to which exosomes had not been administered, and "MSC" is a cell group to which exosomes had been administered. In FIG. 1, the expression level of each gene in "MSC" is represented by a relative value in a case where the expression level of each gene in "Control" is set to 1.

From FIG. 1, as compared with the cell group (Control) to which exosomes had not been administered, the expression levels of four M1 macrophage markers were increased and the expression levels of three markers among the M2 macrophage markers were increased in the cell group (MSC) to which exosomes had been administered.

From this result, in a case where exosomes obtained from a normally cultured MSC had been administered, both M1 type and M2 type macrophages were increased, and it was not possible to shift the polarity to any one of the two types.

Reference Example 3

(Effect of Exosomes Derived from MSC Cultured Under Liver-Damaged Serum on Polarity Change of Macrophage)

Next, the effect of exosomes produced from MSC cultured with the addition of liver damaged mouse serum on the polarity change of macrophages was examined in the in vitro system.

1. Recovery of Exosomes Derived from MSC

Blood was collected from a liver-damaged mouse to which carbon tetrachloride had been intraperitoneally administered for 8 weeks or longer and a healthy mouse, and sera were recovered. Each of the obtained sera was added to MSC derived from mouse bone marrow that had been cultured in advance to be 20 μL per well, and cultured. Next, 24 hours after the addition of serum, the medium was replaced with a serum-free medium, and the cells were further cultured for 24 hours, and 2 mL of the culture supernatant was collected. Next, exosomes were recovered using the same method as in "1." of Reference Example 2.

2. Induction of Macrophage

Figure 2:
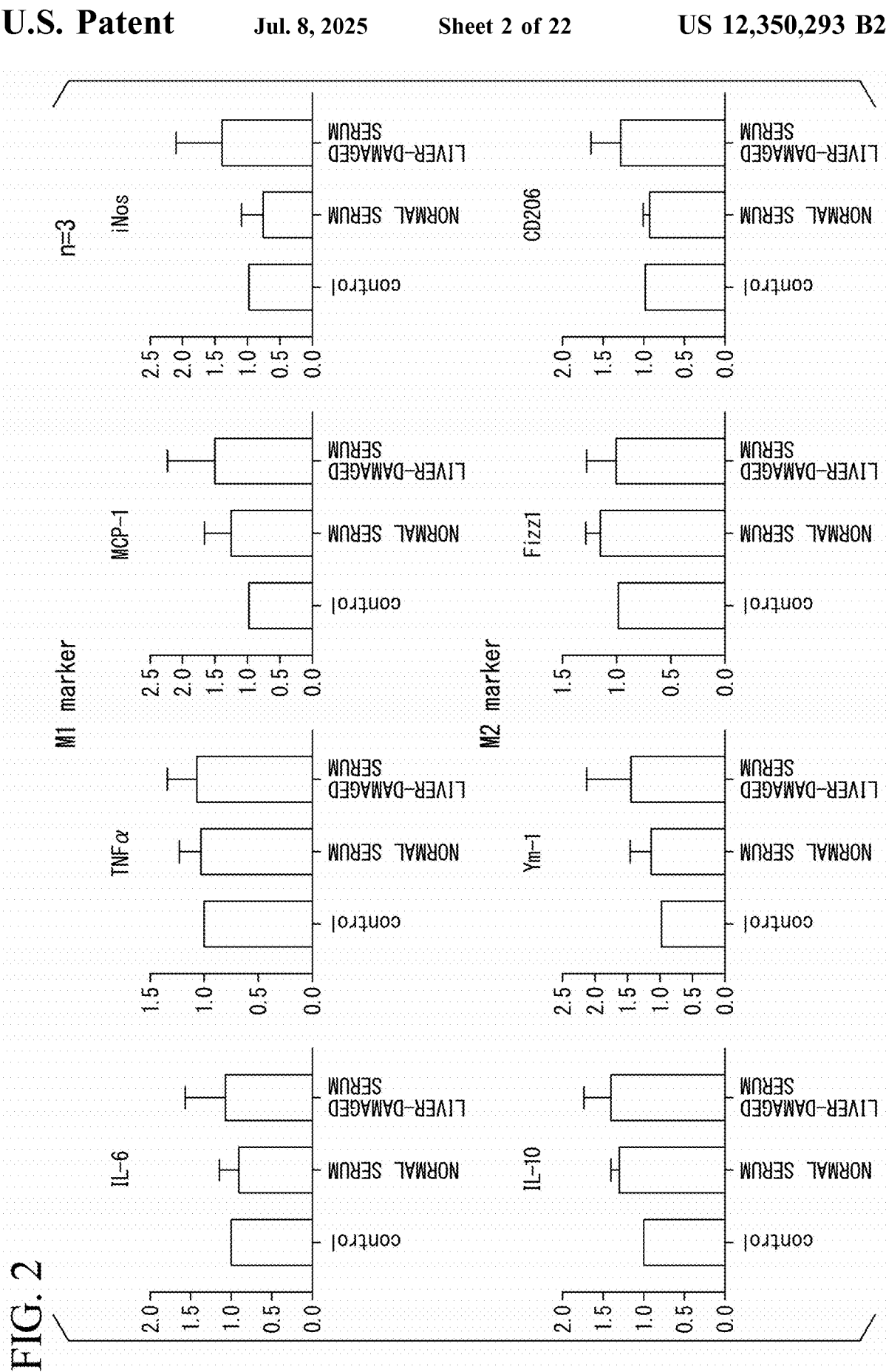
FIG. 2 is a graph showing expression levels of M1 macrophage- and M2 macrophage-specific markers in Reference Example 3.

Next, macrophages ($5 \times 10^6$ cells/well) derived from mouse bone marrow were cultured on a 6-well non-adhesive plate using a medium containing 0.1 g/mL of the obtained exosomes. Using the same method as in "2." of Reference Example 2, the expression levels of the M1 macrophage markers IL-6, TNFα, MCP-1, iNos, and the M2 macrophage markers IL-10, Ym-1, Fizz1, and CD206 were checked by RT-PCR. Each of the primers used for RT-PCR was purchased from QIAGEN. The product number of each primer used is as described in "Reference Example 2". The results are shown in Table 2. In FIG. 2, "Control" is a cell group to which exosomes had not been administered, "NORMAL SERUM" is a cell group to which exosomes produced from MSC cultured with the addition of the serum obtained from a healthy mouse had been administered, and "LIVER-DAMAGED SERUM" is a cell group to which exosomes produced from MSC cultured with the addition of serum obtained from a liver-damaged mouse had been administered. In FIG. 2, the expression level of each gene in "NORMAL SERUM" and "LIVER-DAMAGED SERUM" is represented by a relative value in a case where the expression level of each gene in "Control" is set to 1.

From FIG. 2, as compared with the cell group (Control) to which exosomes had not been administered and the cell group (NORMAL SERUM) to which exosomes produced from MSC cultured with the addition of the serum obtained from a healthy mouse had been administered, the expression levels of four M1 macrophage markers were increased and the expression levels of three markers among the M2 macrophage markers were increased in the cell group (LIVER-DAMAGED SERUM) to which exosomes produced from MSC cultured with the addition of serum obtained from the liver-damaged mouse had been administered.

From this result, in a case where exosomes derived from MSC cultured under liver-damaged serum had been administered, both M1 type and M2 type macrophages were increased as observed in Reference Example 2, and it was not possible to shift the polarity to any one of the two types.

Example 1

(Effect of Exosomes Derived from MSC Stimulated with IFN-γ on Polarity Change of Macrophage)

Next, since a mesenchymal stem cell is known to change expressed factors in response to various environmental changes such as inflammatory stimulation, the effect of exosomes derived from MSC cultured with the addition of inflammatory cytokines on the polarity change of macrophage was examined.

1. Recovery of Exosomes Derived from MSC

MSC was seeded in 6-well dishes in advance and cultured in a serum-free medium until the confluency reached about 80% of the bottom area of each well. Next, the medium was replaced with a serum-free medium containing 100 ng/mL IFN-γ, and culture was carried out. 48 hours after the addition of IFN-γ, the medium was replaced with a serum-free medium, the cells were further cultured for 48 hours, and 2 mL of the culture supernatant was collected. Next, exosomes were recovered using the same method as in "1." of Reference Example 2.

2. Induction of Macrophage

Next, macrophages ($5 \times 10^6$ cells/well) derived from mouse bone marrow were cultured on a 6-well non-adhesive plate using a medium containing 50 ng/mL or 100 ng/mL of the obtained exosomes. Using the same method as in "2." of Reference Example 2, the expression levels of the M1 macrophage markers IL-6, TNFα, MCP-1, iNos, Ly6c, CD40, and the M2 macrophage markers IL-10, Ym-1, Fizz1, and CD206 were checked by RT-PCR. Each of the primers used for RT-PCR was purchased from QIAGEN. Among the primers used, the product numbers of Ly6 and CD40 are as shown below.

Ly6c: QIAGEN QuantiTect Primer Assay QT00247604
CD40: QIAGEN QuantiTect Primer Assay QT00155974

Figure 3:
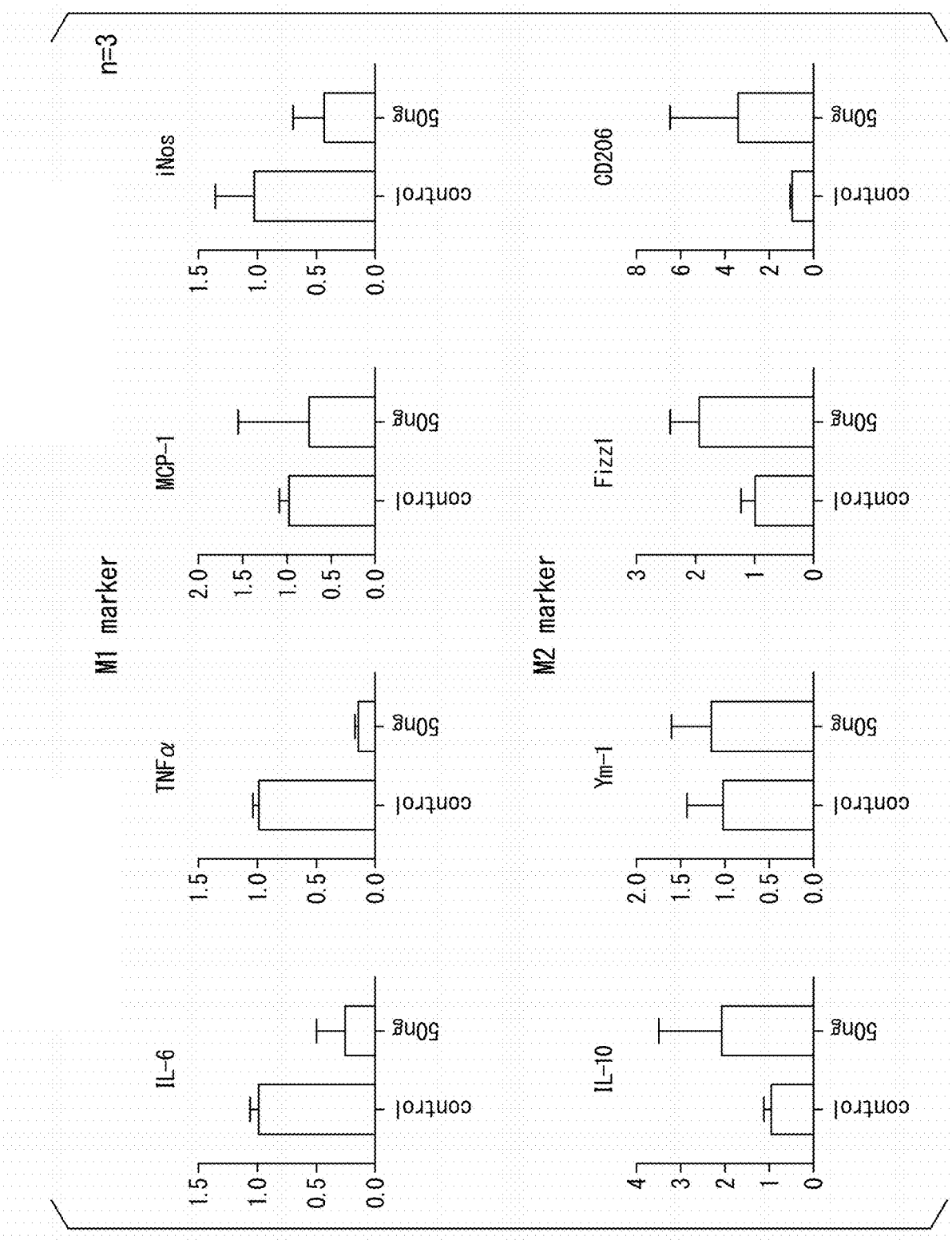
FIG. 3 is a graph showing expression levels of M1 macrophage- and M2 macrophage-specific markers in Example 1.
Figure 4:
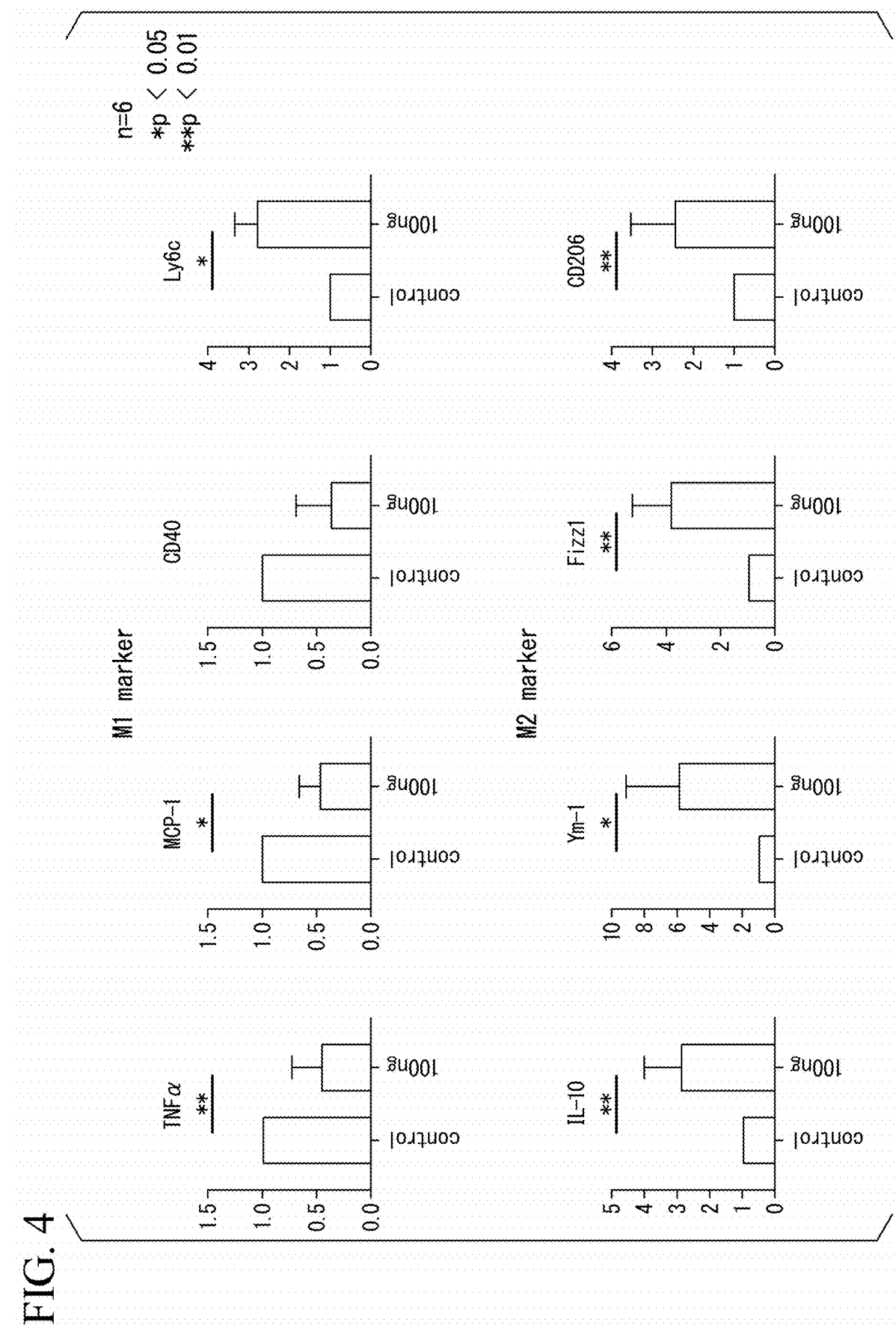
FIG. 4 is a graph showing expression levels of M1 macrophage- and M2 macrophage-specific markers in Example 1.

The results are shown in FIG. 3 (50 ng) and FIG. 4 (100 ng). In FIG. 3 and FIG. 4, "Control" is a cell group to which exosomes had not been administered, "50 ng" is a cell group to which 50 ng/mL exosomes had been administered, and "100 ng" is a cell group to which 100 ng/mL exosomes had been administered. In FIG. 3 and FIG. 4, the expression level of each gene at "50 ng" and "100 ng" is represented by a relative value in a case where the expression level of each gene in "Control" is set to 1.

From FIG. 3 and FIG. 4, as compared with the cell group (Control) to which exosomes had not been administered, the expression levels of four M1 macrophage markers were remarkably decreased and the expression levels of four M2 macrophage markers were significantly increased in the cell group (50 ng/mL or 100 ng/mL) to which 50 ng/ml or 100 ng/ml of exosomes had been administered.

From this result, it was revealed that in a case where exosomes derived from MSC cultured under the stimulation with IFN-γ are administered, it is possible to change the polarity of the macrophage to induce M2 macrophages.

Example 2

(Proteome Analysis and miRNA Analysis of Exosomes Derived from MSC Cultured Under Stimulation with IFN-γ)

Proteins and miRNAs contained in exosomes derived from MSC cultured under the stimulation with IFN-γ were analyzed. Specifically, exosomes produced from MSC derived from human adipose tissue or MSC derived from mouse bone marrow cultured under the stimulation with IFN-γ were extracted and entrusted to the Chemical Evaluation and Research Institute (CERI), Japan, to carry out proteome analysis of the exosome by a shotgun analysis using nanoLC-MS/MS.

In addition, exosomes produced from MSC derived from human adipose tissue cultured under the stimulation with IFN-γ were extracted, and the expression levels of miRNAs in the obtained exosomes were measured by K.K. DNAFORM.

Table 1 shows proteins in the exosome, the expressions of which were increased after the stimulation with IFN-γ, Table 2 shows proteins that were not expressed before the stimulation with IFN-γ but were expressed after the stimulation with IFN-γ, and Table 3 shows proteins of which expression was increased after the stimulation with IFN-γ or proteins which were expressed after the stimulation with IFN-γ, which are common to a human and a mouse.

TABLE 1

|  | Change rate (fold) | Expression level before stimulation | Expression level after stimulation |
| --- | --- | --- | --- |
| Galectin-3-binding protein | 6.5 | 2 | 13 |
| Afamin | 4.8 | 5 | 24 |
| Alpha-1B-glycoprotein | 3.8 | 4 | 15 |
| Hemopexin | 3.1 | 25 | 77 |
| Aminopeptidase N | 2.4 | 18 | 43 |
| Serotransferrin | 2.4 | 17 | 41 |
| Tenascin | 2.1 | 7 | 15 |

TABLE 2

|  | Expression level |
| --- | --- |
| Lactotransferrin | 21 |
| Polymeric immunoglobulin receptor precursor | 13 |
| PLUNC | 13 |
| MHC class I antigen | 10 |
| C20orf114 (BPIF1B1) | 8 |
| Immunoglobulin kappa light chain VLJ region | 8 |
| Major vault protein isoform C, partial | 7 |
| Annexin A1 | 6 |
| Ig alpha-2 chain C region | 6 |
| Type I keratin 16 | 4 |
| Vitamin D-binding protein isoform 1 precursor | 4 |
| Integrin, alpha 2 (CD49B, alpha 2 subunit of VLA-2 receptor), isoform CRAb | 3 |
| M2-type pyruvate kinase | 3 |
| HTRA1 protein | 3 |
| Chain C, Solution Structure Of Human Immunoglobulin M | 3 |
| Keratin 6B, isoform CRA | 3 |
| Leucine-rich alpha-2-glycoprotein 1 | 3 |
| Enolase 1 variant | 2 |
| Platelet-derived growth factor receptor | 2 |
| Chain A, Charged And Uncharged Trnas Adopt Distinct Conformations | 2 |
| Complement cytolysis inhibitor precursor | 2 |
| Immunoglobulin heavy chain | 2 |

TABLE 3

Aminopeptidase N (CD13)
Serotransferrin
Hemoglobin subunit alpha
Lactadherin
Basement membrane-specific heparan sulfate proteoglycan core protein
Collagen alpha-1 (I) chain
Histone H4
Annexin A2

TABLE 3-continued

Elongation factor 1-alpha 1
Galectin-3-binding protein
Annexin A6
Annexin A5
Annexin A1
Glyceraldehyde-3-phosphate dehydrogenase
Pyruvate kinase PKM
Fatty acid synthase
Alpha-enolase
Keratin, type I cytoskeletal 16
Tubulin alpha-1B chain
Programmed cell death 6-interacting protein Table 4 shows miRNAs in the exosomes, the expression levels of which were increased 4-fold or more after the stimulation with IFN-γ, and Table 5 shows miRNAs in the exosomes, the expression levels of which were decreased to ¼ or less.

TABLE 4

| miR1291 | miR1247  | miR1-2  | miR148B  | miR185  | miR6858 | miR27A   | miR4492 |
|---------|----------|---------|----------|---------|---------|----------|---------|
| miR3651 | mi7-3    | miR339  | miR340   | miR15A  | miR551A | miR1296  | miR3907 |
| miR184  | miR7-1   | miR145  | miR3648-2| miR589  | miR625  | miR377   | miR4321 |
| miR664A | miR101-2 | miR92B  | miR4792  | miR532  | miR1290 | miR376A2 | miR6785 |
| miR1-1  | miR7641-2| miR328  | miR3648-1| miR193B | miR3664 | miR376A1 | miR7-2  |

TABLE 5

| miR205  | miR196B  | miR1262  | miR200C  | miR26A1 | miR140   | miR320D1 | miR892C |
|---------|----------|----------|----------|---------|----------|----------|---------|
| miR224  | miR20A   | miR941-3 | miR542   | miR26A2 | miR361   | miR941-2 | miR3621 |
| miR425  | miR218-1 | miR3615  | miR501   | miR5687 | miR200B  | miR320D2 | miR3182 |
| miR151A | miR218-2 | miR337   | miR802   | miR375  | miR629   | miR3613  | miR23C  |
| miR708  | miR660   | miR142   | miR885   | miR17   | miR190A  | miR30B   | miR3195 |
| miR31   | miR1468  | miR141   | miR1268B | miR93   | miR486-1 | miR429   | miR19B2 |
| miR1307 | miR24-2  | miR572   | miR4500  | miR149  | miR941-5 | miR378A  | miR19B1 |
| miR374A | miR24-1  | miR941-1 | miR6126  | miR15B  | miR486-2 | miR200A  | miR935  |
| miR186  | miR576   | miR128-1 | miR7845  | miR1180 | miR671   | miR183   |         |
| miR23B  | miR941-4 | miR28    | miR632   |         |          |          |         |

From Table 1 to Table 5, it was confirmed that various proteins and miRNAs were expressed by the stimulation with IFN-γ and contained in the exosome. It was speculated that among these proteins and miRNAs, not one single factor but a combination of a plurality of factors affects the polarity change of macrophage.

Example 3

Figure 5:
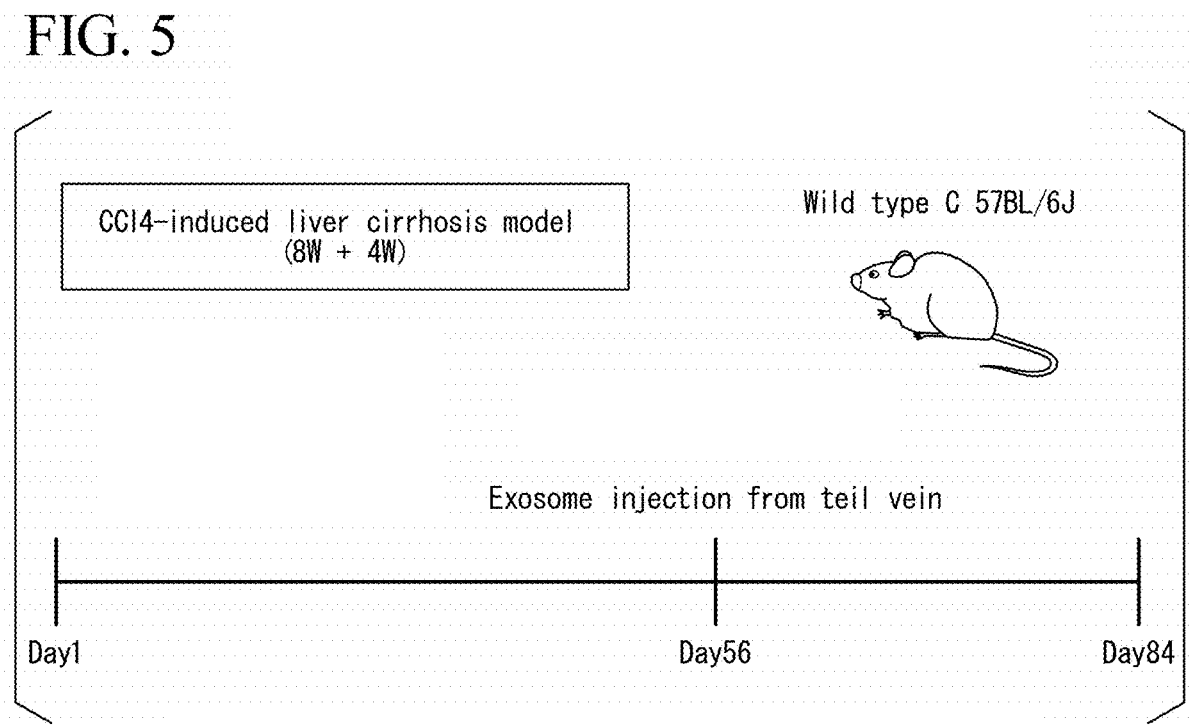
FIG. 5 is a diagram schematically showing a test flow in Example 3.

(Exosome Administration Test to Liver Damage Model Mouse)
1. Exosome Administration to Liver Damage Model Mouse Carbon tetrachloride was intraperitoneally administered to a wild-type mouse (C57BL/6J) for 8 weeks to prepare a liver damage model mouse. Next, any one of the following (1) to (7) was administered to the tail vein at the 8th week (on the 56th day), and the mouse was further reared for 4 weeks (see FIG. 5).
  (1) PBS;
  (2) Normally cultured mouse MSC ($1\times10^6$ cells);
  (3) Mouse MSC ($1\times10^6$ cells) cultured under the stimulation with IFN-γ;
  (4) Exosomes (2 μg) recovered from a normally cultured mouse MSC;
  (5) Exosomes (2 μg) recovered from mouse MSC cultured under the stimulation with IFN-γ;
  (6) Normally cultured human MSC ($1\times10^6$ cells);
  (7) Human MSC ($1\times10^6$ cells) cultured under the stimulation with IFN-γ

Figure 6:
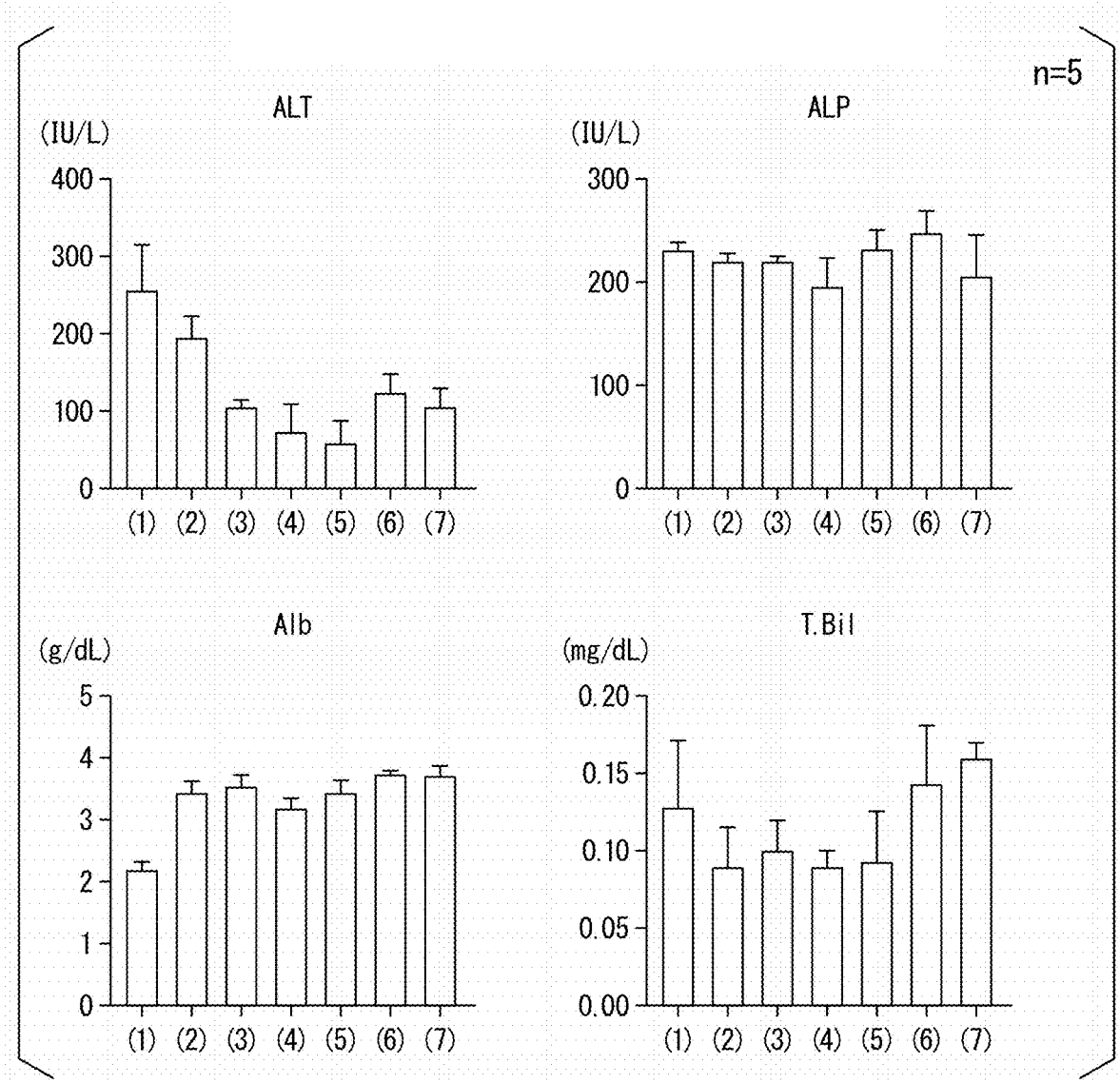
FIG. 6 is a graph showing the content of each component in serum collected from each mouse group in Example 3.
Figure 7:
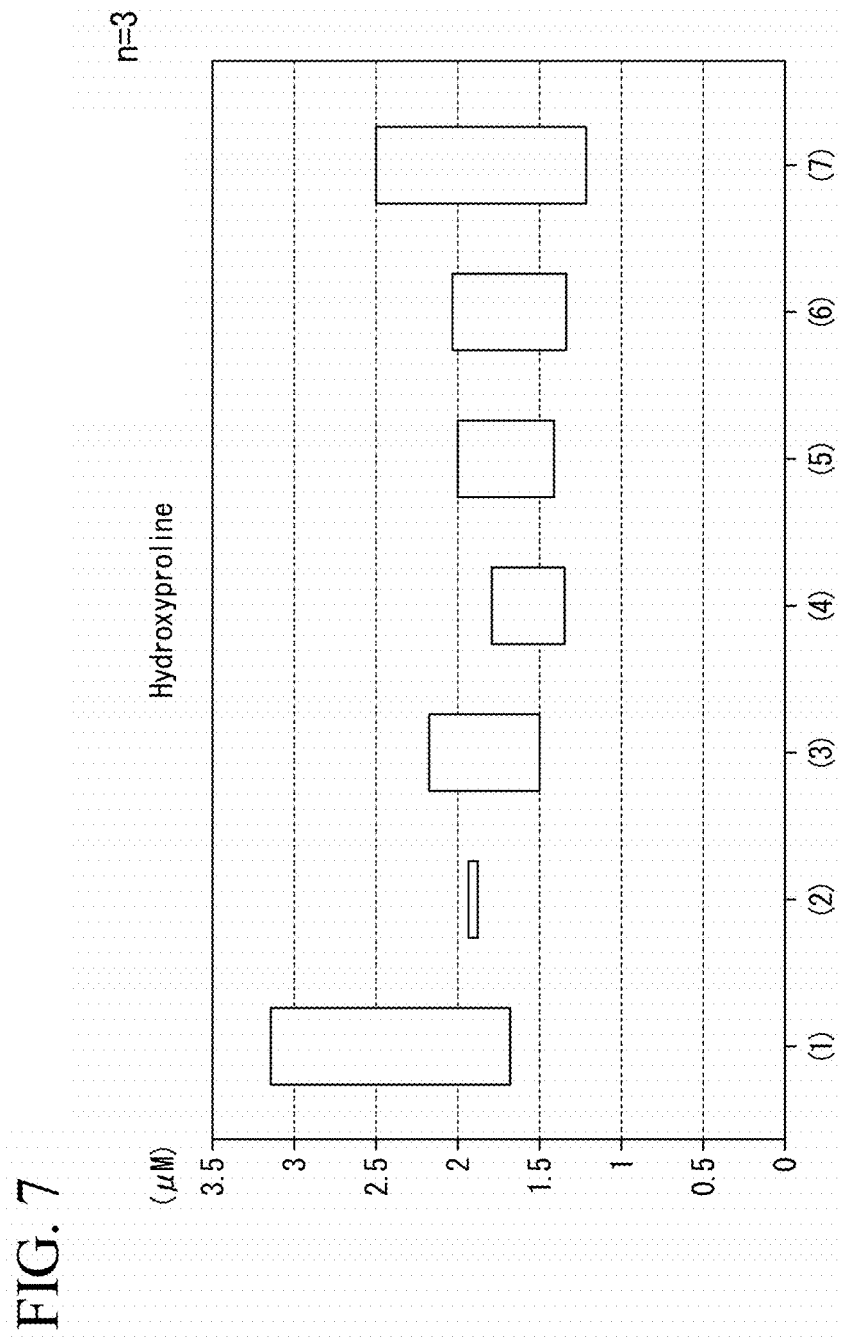
FIG. 7 is a graph showing the content of hydroxyproline in serum collected from each mouse group in Example 3.

Blood was collected from the reared mouse, serum was recovered, and the measurement of the amount of alanine aminotransferase (ALT), the measurement of the amount of alkaline phosphatase (ALP), the measurement of the amount of albumin (Alb), and the measurement of the total amount of bilirubin (T. Bil) in the serum were entrusted to Oriental Yeast Co., Ltd., and the amount of hydroxyproline was measured using the QuickZyme Hydroxyproline Kit (QZB-HYPRO1). Here, ALT is a hepatocyte damage marker, and hydroxyproline is a fibrosis marker. The results are shown in FIG. 6 (ALT, ALP, Alb, and T. Bil) and FIG. 7 (hydroxyproline). In FIG. 6 and FIG. 7, (1) to (7) correspond to the mouse groups to which the above (1) to (7) had been administered, respectively.

From FIG. 6, there were no significant differences in the amounts of ALP, Alb, and T. Bil between the groups; however, the value of ALT, which is a hepatocyte damage marker, was remarkably decreased in the mouse group to which the exosomes recovered from the mouse MSC cultured under the stimulation with IFN-γ had been administered as compared with other mouse groups.

In addition, from FIG. 7, it can be seen that the amount of hydroxyproline, which is a fibrosis marker, also tends to be decreased in the mouse group administered with the exosomes recovered from the mouse MSC cultured under the stimulation with IFN-γ as compared with other mouse groups.

From the above, it was suggested that liver damage can be ameliorated by administering the exosomes recovered from the MSC cultured under the stimulation with IFN-γ.

Example 4

(Effect of Exosomes Derived from Human MSC Stimulated with IFN-γ on Polarity Change of Mouse Macrophage)

Next, the effect of exosomes derived from a human MSC cultured with the addition of inflammatory cytokines on the polarity change of the mouse macrophage was examined.
1. Recovery of Exosomes Derived from Human MSC MSC derived from human adipose tissue was seeded in 6-well dishes in advance and cultured in a serum-free medium until the confluency reached about 80% of the bottom area of each well. Next, the medium was replaced with a serum-free medium containing 100 ng/mL IFN-γ, and culture was carried out. 48 hours after the addition of IFN-γ, the medium was replaced with a serum-free medium, the cells were further cultured for 48 hours, and 2 mL of the culture supernatant was collected. Next, exosomes were recovered using the same method as in "1." of Reference Example 2.

2. Induction of Macrophage

Figure 8:
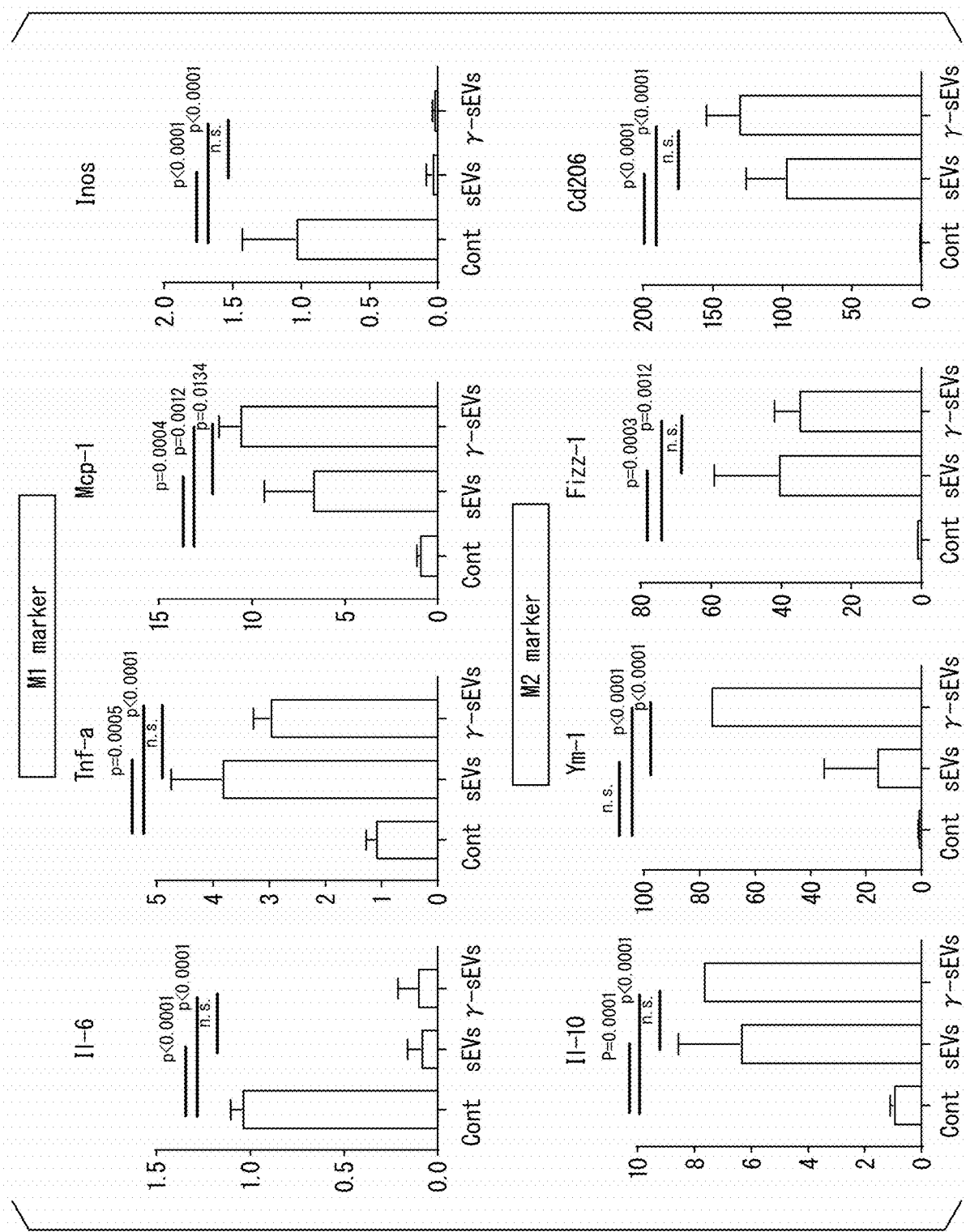
FIG. 8 is a graph showing expression levels of M1 macrophage- and M2 macrophage-specific markers in Example 4.

Next, mouse macrophages ($5 \times 10^6$ cells/well) were cultured on a 6-well non-adhesive plate using a medium containing 100 ng/nL of the obtained exosomes. Hereinafter, this cell group may be referred to as a γ-sEVs group. As a control, a cell group (a Control group) to which exosomes had not been administered was prepared. In addition, as a reference, a cell group (the sEVs group) to which exosomes recovered from a normally cultured human MSC without the stimulation with IFN-γ had been administered was also prepared. Using the same method as in "2." of Reference Example 2, the expression levels of the M1 macrophage markers IL-6, TNFα, MCP-1, iNos, and the M2 macrophage markers IL-10, Ym-1, Fizz1, and CD206 were checked by RT-PCR. Each of the primers used for RT-PCR was purchased from QIAGEN. The results are shown in Table 8. In FIG. 8, the expression level of each gene in the "sEVs group" and the "γ-sEVs group" is represented by a relative value in a case where the expression level of each gene in the "Control group (Cont group)" is set to 1.

From FIG. 8, as compared with the cell group (Control) to which exosomes had not been administered, the expression levels of the M1 macrophage markers were remarkably decreased and the expression levels of the M2 macrophage markers were significantly increased in the cell group to which exosomes recovered from human MSC cultured under the stimulation with IFN-γ had been administered.

From this result, it was confirmed that in a case where exosomes derived from a human MSC cultured under the stimulation with IFN-γ are administered, it is possible to change the polarity of the mouse macrophage to induce an M2 macrophage.

Example 5

(Proteome Analysis and miRNA Analysis of Exosomes Derived from Human MSC Cultured Under Stimulation with IFN-γ)

Proteins and miRNAs contained in exosomes derived from MSC derived from human adipose tissue, where the MSC had been cultured under the stimulation with IFN-γ or cultured normally, were analyzed. Specifically, exosomes produced from MSC derived from human adipose tissue cultured under the stimulation with IFN-γ were extracted and entrusted to the Chemical Evaluation and Research Institute (CERI), Japan, to carry out proteome analysis of the exosome by a shotgun analysis using nanoLC-MS/MS.

In addition, exosomes produced from MSC derived from human adipose tissue, where the MSC had been cultured under the stimulation with IFN-γ or cultured normally were extracted, and the expression levels of miRNAs in the obtained exosomes were measured by K.K. DNAFORM. The results of the proteome analysis are shown in Table 6-1 and Table 6-2, and the results of the miRNA analysis are shown in Table 7 and Table 8. In Table 6-1 and Table 6-2, the "sEVs" column shows the expression levels of proteins in the exosomes derived from the human MSC normally cultured without the stimulation with IFN-γ. The "γ-sEVs" column shows the expression levels of proteins in the exosomes derived from the human MSC cultured under the stimulation with IFN-γ. The miRNAs shown in Table 7 were also expressed in the exosomes derived from the human MSC normally cultured without the stimulation with IFN-γ, and expression levels thereof were maintained high even after the stimulation with IFN-γ. The miRNAs shown in Table 8 are miRNAs of which the expression level in the exosome increased after the stimulation with IFN-γ.

TABLE 6-1

| Bio View: Identified Proteins (77) | Expression level | |
|---|---|---|
| | sEVs | γ-sEVs |
| Collagen alpha-3 (VI) chain | 1600 | 1233 |
| Fibronectin | 499 | 319 |
| Collagen alpha-1 (VI) chain | 424 | 341 |
| Collagen alpha-2 (VI) chain | 212 | 154 |
| Serum albumin | 138 | 209 |
| Keratin, type II cytoskeletal 1 | 65 | 69 |
| Haptoglobin | 43 | 67 |
| Hemopexin | 25 | 77 |
| Keratin, type I cytoskeletal 10 | 45 | 38 |
| Aminopeptidase N | 18 | 43 |
| Serotransferrin | 17 | 41 |
| Collagen alpha-2 (I) chain | 21 | 25 |
| Actin, cytoplasmic 1 | 19 | 22 |
| Keratin, type II cytoskeletal 2 epidermal | 23 | 14 |
| Afamin | 5 | 24 |
| Hemoglobin subunit alpha | 12 | 13 |
| Transforming growth factor-beta-induced protein ig-h3 | 20 | 12 |
| Tenascin | 7 | 15 |
| Alpha-1B-glycoprotein | 4 | 15 |
| Histone H2A type 1-B/E | 21 | 6 |
| Keratin, type I cytoskeletal 9 | 13 | 16 |
| Dynein heavy chain 3, axonemal | 4 | 0 |
| Versican core protein | 7 | 13 |
| Lactadherin | 12 | 13 |
| Basement membrane-specific heparan sulfate proteoglycan core protein | 6 | 4 |
| Lactotransferrin | 0 | 24 |
| Trypsin-2 | 10 | 2 |

TABLE 6-1-continued

| Bio View: Identified Proteins (77) | Expression level | |
|---|---|---|
| | sEVs | γ-sEVs |
| BPI fold-containing family A member 1 | 0 | 17 |
| Collagen alpha-1 (I) chain | 7 | 9 |
| Histone H4 | 17 | 5 |
| Alpha-2-macroglobulin | 6 | 9 |
| Polymeric immunoglobulin receptor | 0 | 17 |
| 5'-nucleotidase | 5 | 8 |
| Annexin A2 | 7 | 9 |
| Integrin beta-1 | 0 | 7 |
| Elongation factor 1-alpha 1 | 6 | 7 |
| Galectin-3-binding protein | 2 | 13 |
| HLA class I histocompatibility antigen, B-49 alpha chain | 0 | 15 |
| Heat shock 70 kDa protein 1A | 8 | 0 |
| Hemoglobin subunit beta | 3 | 5 |
| Immunoglobulin heavy constant alpha 1 | 0 | 10 |

TABLE 6-2

| Bio View: Identified Proteins (77) | Expression level | |
|---|---|---|
| | sEVs | γ-sEVs |
| Annexin A6 | 6 | 4 |
| BPI fold-containing family B member 1 | 0 | 9 |
| Major vault protein | 0 | 7 |
| Annexin A5 | 7 | 0 |
| Annexin A1 | 0 | 8 |
| Pecanex-like protein 3 | 0 | 2 |
| Immunoglobulin kappa constant | 0 | 9 |
| Histone H2B type F-S | 5 | 0 |
| Ubiquitin-60S ribosomal protein L40 | 5 | 5 |
| Glyceraldehyde-3-phosphate dehydrogenase | 5 | 2 |
| Pyruvate kinase PKM | 3 | 3 |
| Periostin | 5 | 3 |
| Alpha-2-HS-glycoprotein | 0 | 6 |
| Keratin, type II cytoskeletal 6C | 0 | 5 |
| Integrin alpha-2 | 0 | 4 |
| Fatty acid synthase | 2 | 0 |
| Protein S100-A9 | 0 | 6 |
| Deleted in malignant brain tumors 1 protein | 0 | 4 |
| E3 ubiquitin-protein ligase SHPRH | 3 | 0 |
| Alpha-enolase | 0 | 3 |
| N-acetylmuramoyl-L-alanine amidase | 0 | 2 |
| Keratin, type I cytoskeletal 16 | 0 | 4 |
| Vitamin D-binding protein | 0 | 5 |
| Tubulin alpha-1B chain | 0 | 3 |
| Serine protease HTRA1 | 0 | 5 |
| Protein S100-A8 | 0 | 5 |
| Programmed cell death 6-interacting protein | 2 | 0 |
| Collagen alpha-1 (III) chain | 2 | 0 |
| Platelet-derived growth factor receptor beta | 0 | 2 |
| Leucine-rich alpha-2-glycoprotein | 0 | 4 |
| Immunoglobulin gamma-1 heavy chain | 0 | 3 |
| Clusterin | 0 | 3 |
| Tryptophan—tRNA ligase, cytoplasmic | 0 | 2 |
| Plasma protease C1 inhibitor | 0 | 2 |
| Prolyl endopeptidase FAP | 0 | 2 |
| Immunoglobulin lambda-1 light chain | 0 | 2 |

TABLE 7

| | | | | | |
|---|---|---|---|---|---|
| MIRLET7B | MIR21 | MIR125B1 | MIR125B2 | MIRLET7I | MIR221 |
| MIR199A1 | MIR199A2 | MIR155 | MIR199B | MIR122 | MIR16-1 |
| MIR16-2 | MIR125A | MIRLET7A3 | MIRLET7A1 | MIRLET7A2 | MIRLET7F2 |
| MIRLET7F1 | MIR29A | | | | |

TABLE 8

| | | | | | |
|---|---|---|---|---|---|
| MIRLET7B | MIR21 | MIR125B1 | MIR125B2 | MIRLET7I | MIR221 |
| MIR199A1 | MIR199A2 | MIR155 | MIR199B | MIR122 | MIR16-1 |

TABLE 8-continued

| MIR16-2 | MIR125A | MIRLET7A3 | MIRLET7A1 | MIRLET7A2 | MIRLET7F2 |
|---|---|---|---|---|---|
| MIRLET7F1 | MIR29A | | | | |

From Table 6-1 to Table 8, it was confirmed that various proteins and miRNAs were expressed in the human MSC by the stimulation with IFN-γ and contained in the exosome derived from the human MSC.

Next, regarding five proteins (Annexin A1, Lactadherin, Lactotransferrin, Galectin-3 binding protein, and Aminopeptidase N) known to be related to the macrophage among the protein groups shown in Table 6-1 and Table 6-2, the effect of each protein on the polarity change of the mouse macrophages was examined.

Figure 9A:
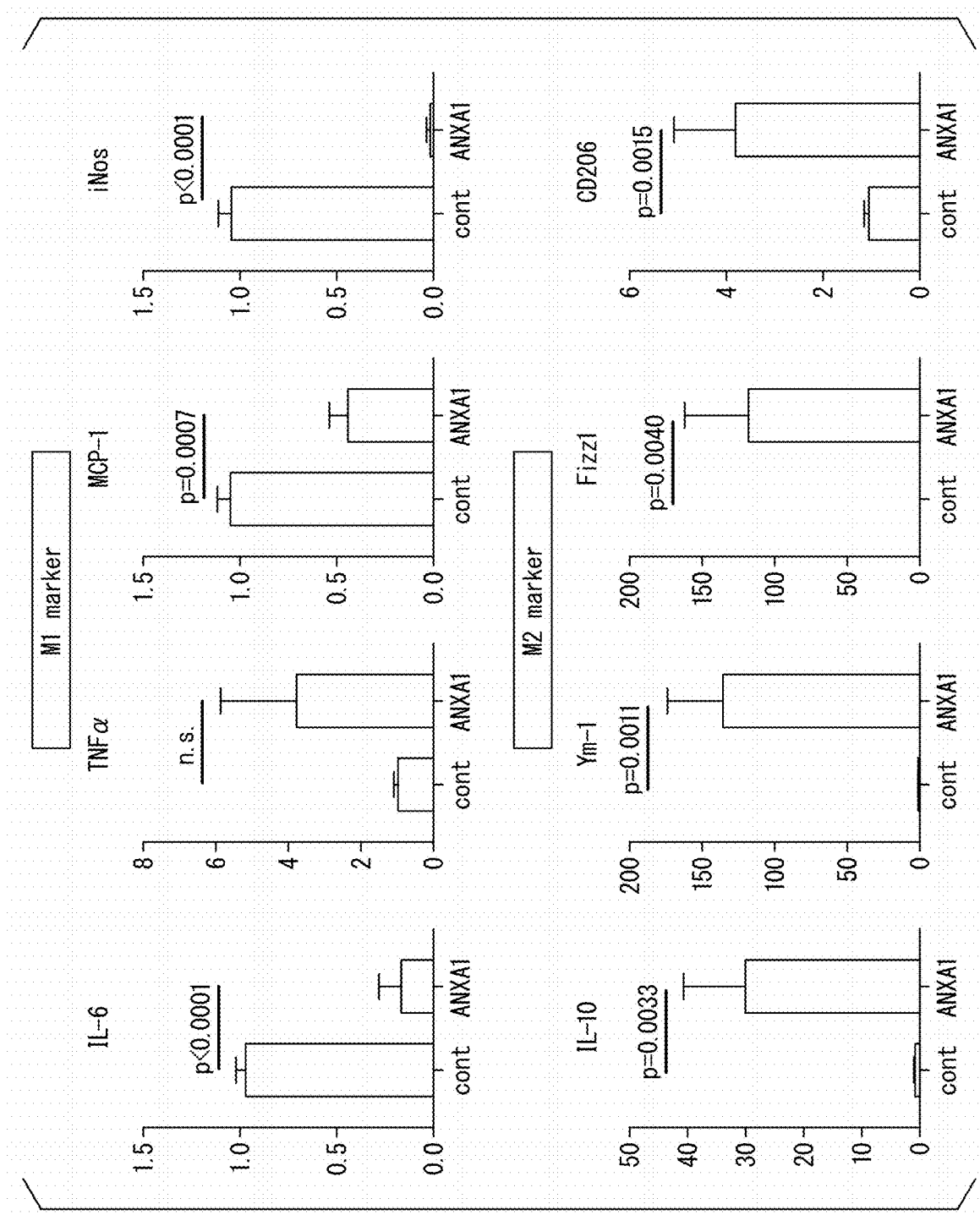
FIG. 9A is a graph showing expression levels of M1 macrophage- and M2 macrophage-specific markers in Example 5.
Figure 9B:
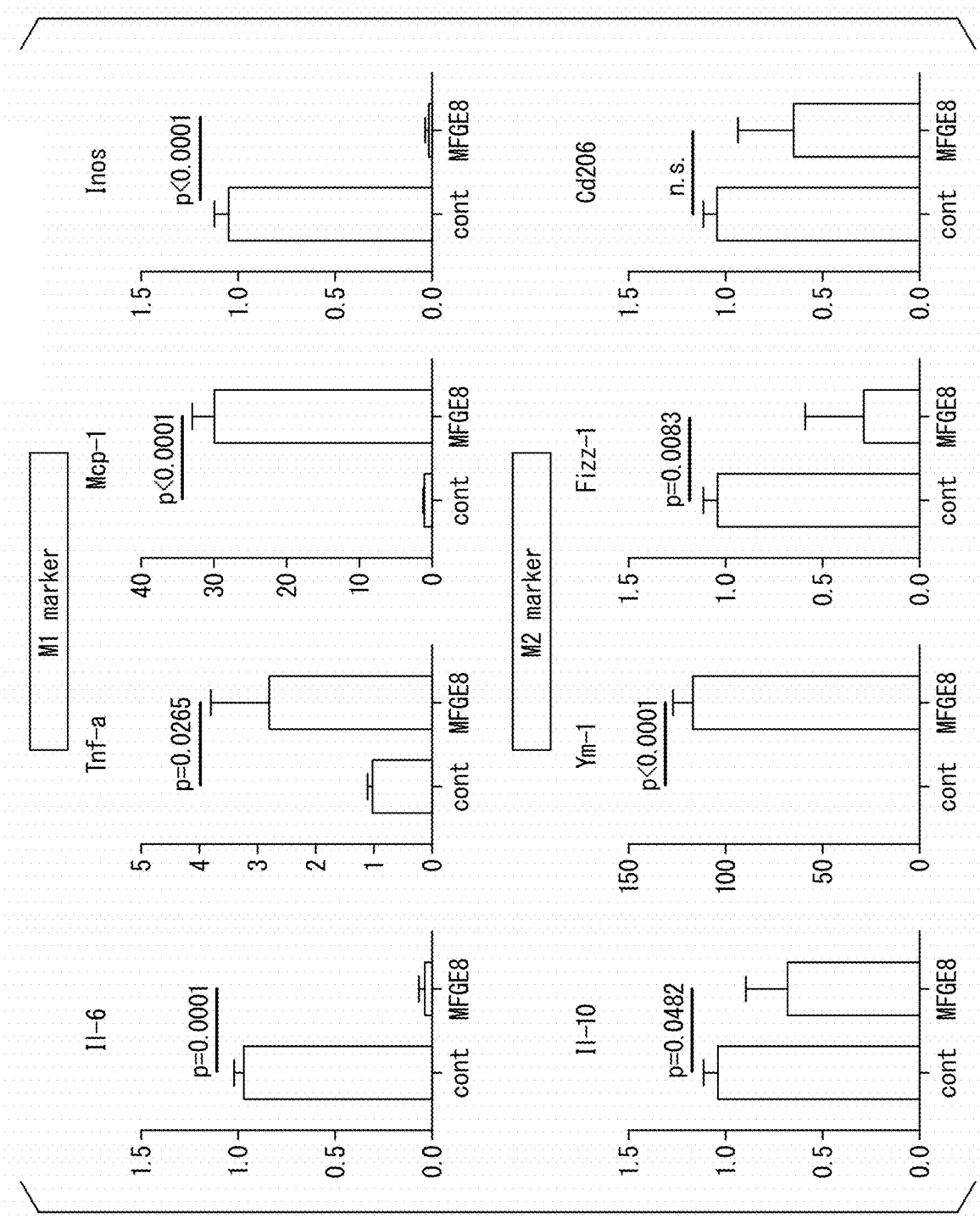
FIG. 9B is a graph showing expression levels of M1 macrophage- and M2 macrophage-specific markers in Example 5.
Figure 9C:
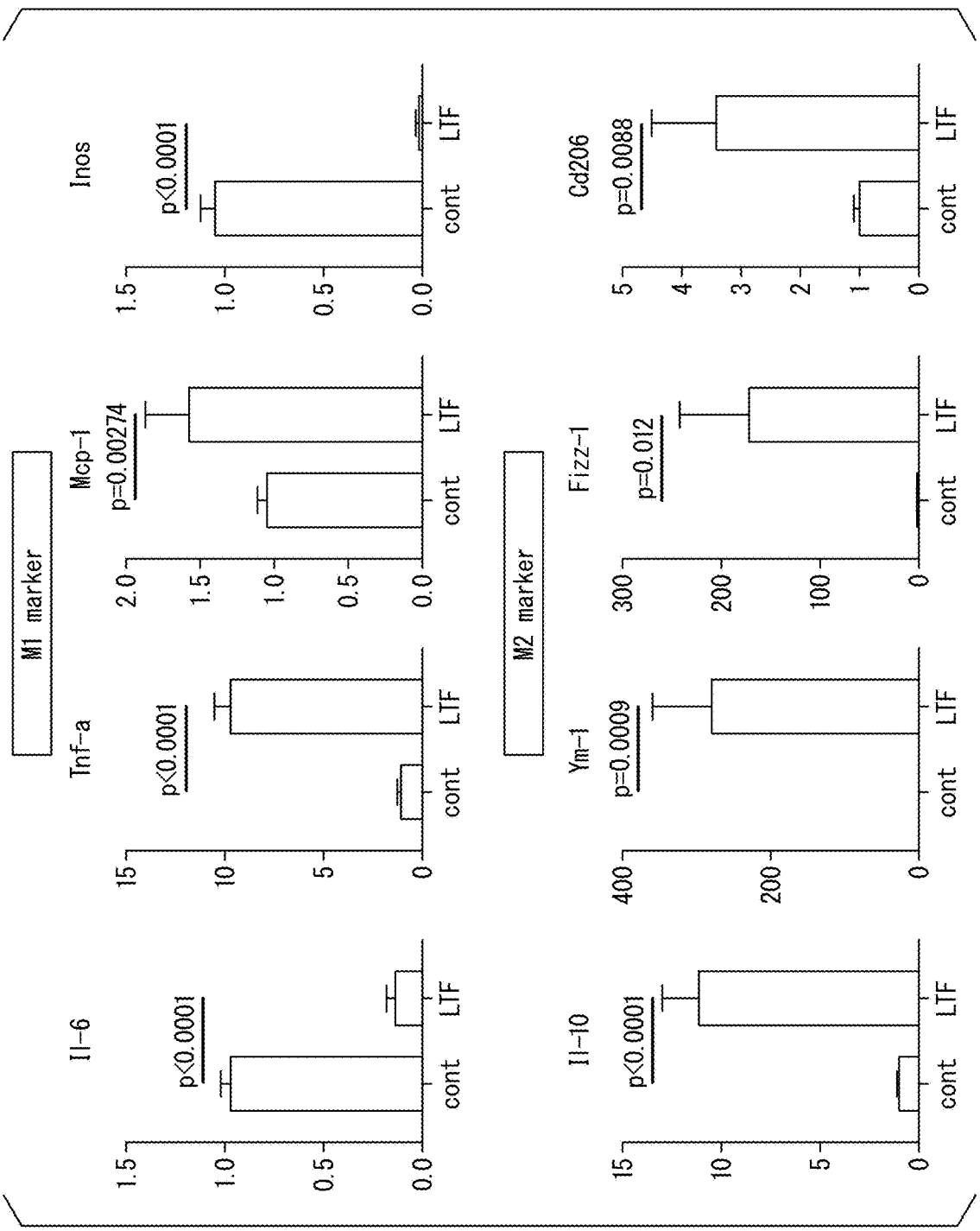
FIG. 9C is a graph showing expression levels of M1 macrophage- and M2 macrophage-specific markers in Example 5.
Figure 9D:
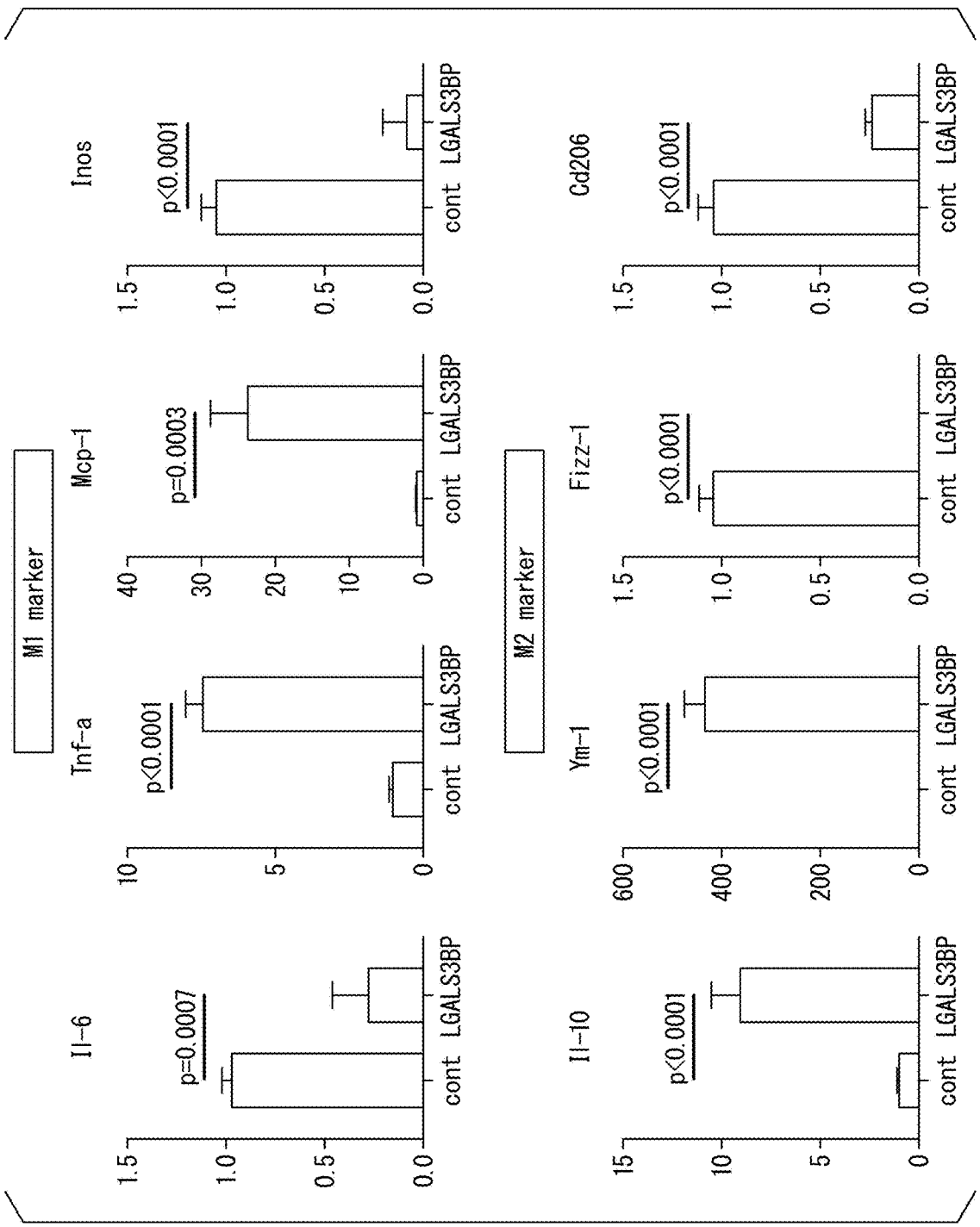
FIG. 9D is a graph showing expression levels of M1 macrophage- and M2 macrophage-specific markers in Example 5.
Figure 9E:
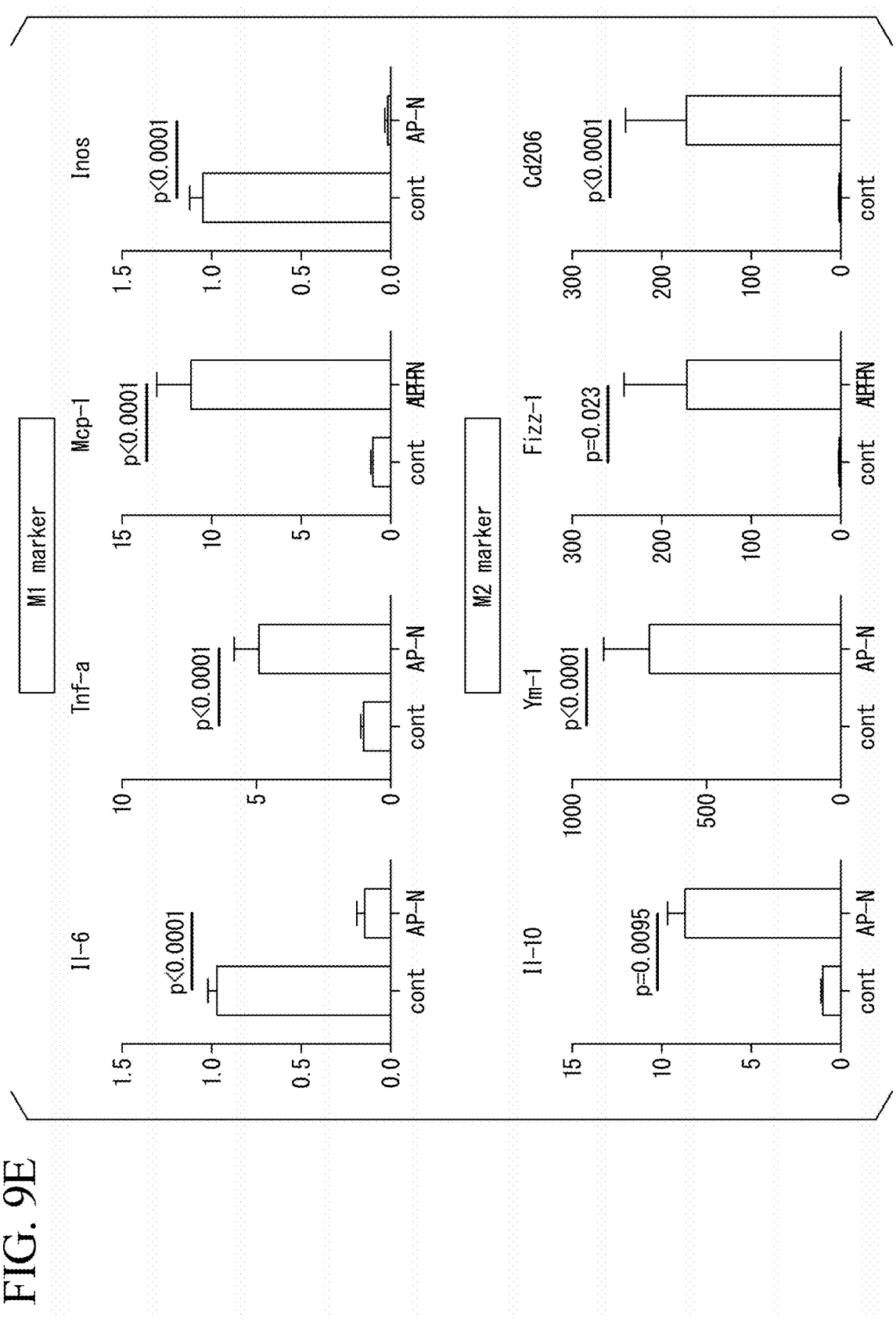
FIG. 9E is a graph showing expression levels of M1 macrophage- and M2 macrophage-specific markers in Example 5.

Specifically, mouse macrophages ($5\times10^6$ cells/well) were cultured on a 6-well non-adhesive plate using a medium containing each of the proteins (Annexin A1, Lactadherin, Lactotransferrin, Galectin-3 binding protein, and Aminopeptidase N) at the concentrations shown in (1) to (5) below.
  (1) Annexin A1: manufactured by Abcam plc, trade name: "Recombinant Human Annexin A1 protein", concentration in medium: 100 ng/mL
  (2) Lactadherin: manufactured by R&D Systems Inc., product number 2767-MF-050, trade name: "Recombinant Human MFGE8 Protein", concentration in medium: 100 ng/mL
  (3) Lactotransferrin: manufactured by Abcam plc, trade name: "Recombinant Human Lactoferrin protein", concentration in medium: 0.1 ng/mL
  (4) Galectin-3 binding protein: manufactured by Aviva Systems Biology, trade name: "LGALS3BP Recombinant Protein (OPCD04925)", concentration in medium: 1 ng/mL
  (5) Aminopeptidase N: manufactured by R&D Systems Inc., trade name "Recombinant Human Aminopeptidase N/CD13", concentration in medium: 100 ng/mL As a control, a cell group (a Control group) to which each protein had not been added was prepared. Using the same method as in "2." of Reference Example 2, the expression levels of the M1 macrophage markers IL-6, TNFα, MCP-1, iNos, and the M2 macrophage markers IL-10, Ym-1, Fizz1, and CD206 were checked by RT-PCR. Each of the primers used for RT-PCR was purchased from QIAGEN. The results are shown in FIG. 9A (Annexin A1, abbreviated as ANXA1), FIG. 9B (Lactadherin, also referred to as MFGE8), FIG. 9C (Lactotransferrin, abbreviated as LTF), FIG. 9D (Galectin-3 binding protein, abbreviated as LCALS3BP), and FIG. 9E (Aminopeptidase N, abbreviated as AP-N). In FIG. 9A to FIG. 9E, the expression level of each gene in the cell group cultured in the presence of each protein is represented by a relative value in a case where the expression level of each gene in the "Control group (Cont group)" is set to 1.

From FIG. 9A to FIG. 9E, it was revealed that the polarity of the mouse macrophage was changed by adding each protein.

Example 6

(Exosome Administration Test to Liver Damage Model Mouse)
1. Exosome Administration to Liver Damage Model Mouse
  Carbon tetrachloride was intraperitoneally administered to a CX₃CR1-EGFP mouse for 8 weeks to prepare a liver damage model mouse. The CX₃CR1-EGFP mouse is a mouse in which macrophages derived from other than the liver express a green fluorescent substance (GFP). Next, any one of the following (1) to (3) was administered to the tail vein at the 8th week (on the 56th day), and the mouse was further reared for 24 hours.
  (1) PBS;
  (2) Exosomes (2 μg) recovered from a normally cultured human MSC (hereinafter, may be referred to as "sEVs group");
  (3) Exosomes (2 μg) recovered from a human MSC cultured under the stimulation with IFN-γ (hereinafter, may be referred to as "γ-sEVs group")

Figure 10A:
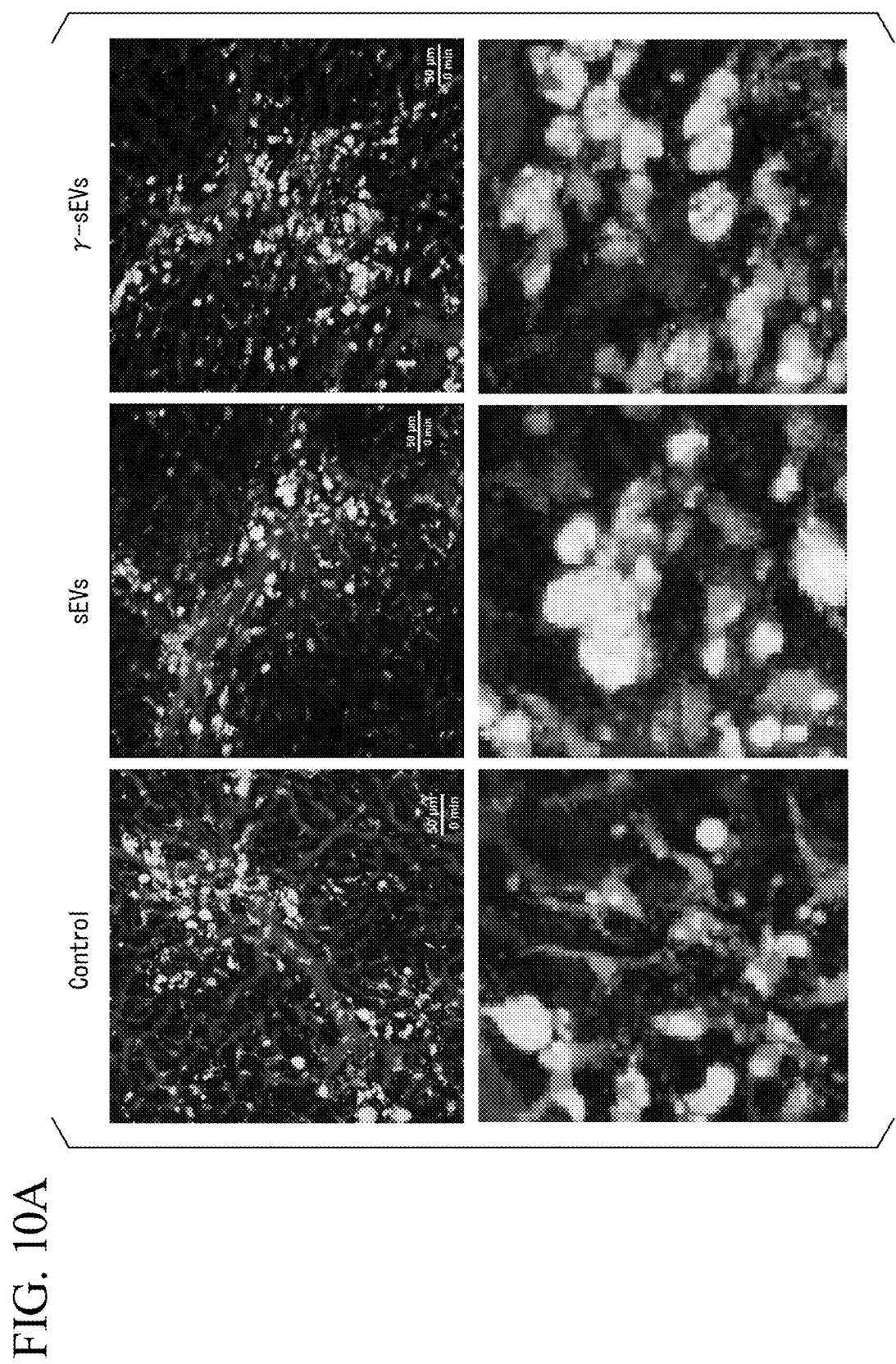
FIG. 10A is fluorescence images of a liver exposed under anesthesia in each mouse group in Example 6 (the green fluorescence indicates macrophages, and the yellow substance indicates necrosis of hepatocytes). In the upper fluorescence images, the scale bar is 50 μm. The lower fluorescence images are magnified images of the upper fluorescence images, respectively.

24 hours after the administration, rhodamine B-conjugated dextran (M.W. 70,000) was administered to the mouse by intravenous injection to the tail vein to stain blood vessels. Next, the mouse was anesthetized and a small incision was made in the peritoneum to expose the liver, which was subsequently observed under a two-photon excitation microscope. The results are shown in FIG. 10A. In FIG. 10A, dead cells were observed by autofluorescence (yellow color). In addition, in FIG. 10B, the graph on the left is a graph showing the number of macrophage cells attached to hepatocyte necrotic tissue in an image in which approximately ¼ of a circle having a diameter of 100 μm is occupied by the hepatocyte necrotic tissue. That is, it is a graph showing how many macrophages participate in the processing of foreign matter (the necrotic tissue). The graph on the right is a graph showing the number of macrophage cells that have moved to and accumulated in the hepatocyte necrotic portion in an image section obtained by dividing the observation image into ¼.

Figure 10B:
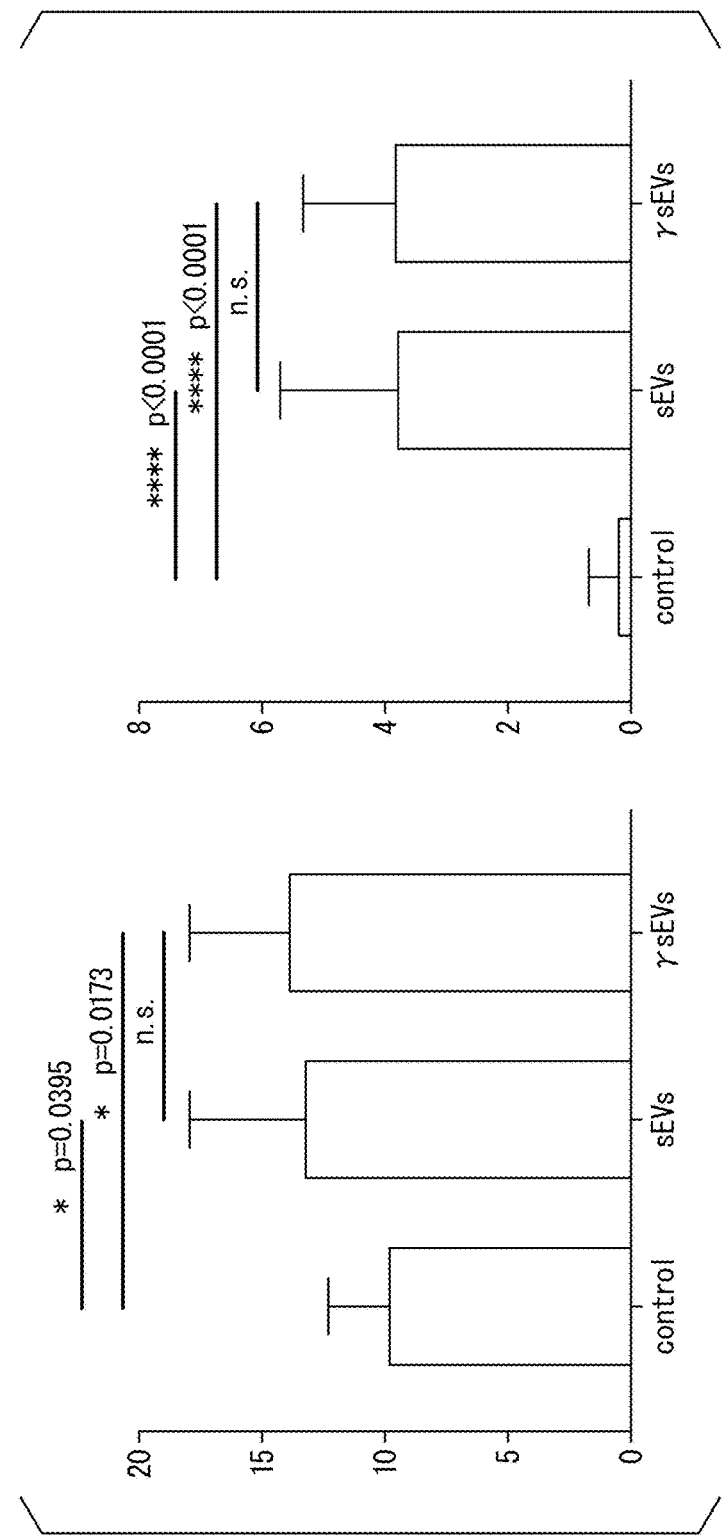
In FIG. 10B, the graph on the left is a graph showing the number of macrophage cells attached to hepatocyte necrotic tissue in an image in which approximately ¼ of a circle having a diameter of 100 m is occupied by the hepatocyte necrotic tissue. The graph on the right is a graph showing the number of macrophage cells that have moved to and accumulated in the hepatocyte necrotic portion in an image section obtained by dividing the observation image into ¼.

From FIG. 10A and FIG. 10B, it was revealed that exosomes changed the morphology of macrophages, and a large number of macrophages accumulated near the hepatocyte necrotic tissue and in the damaged part of blood vessels.

Example 7

Figure 11A:
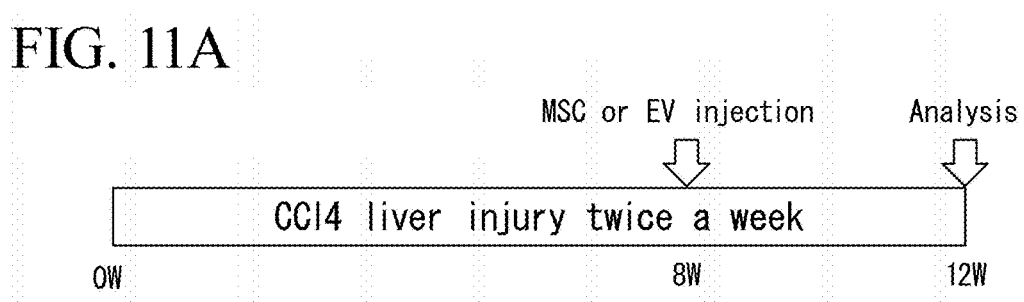
FIG. 11A is a diagram schematically showing a test flow in Example 7.

(Exosome Administration Test to Liver Damage Model Mouse)
1. Exosome Administration to Liver Damage Model Mouse
  Carbon tetrachloride was intraperitoneally administered to a wild-type mouse (C57BL/6J) for 8 weeks to prepare a liver damage model mouse. Next, any one of the following (1) to (7) was administered to the tail vein at the 8th week (on the 56th day), and the mouse was further reared for 4 weeks (see FIG. 11A).
  (1) PBS (hereinafter sometimes referred to as "Control group");
  (2) Normally cultured human MSC ($1\times10^6$ cells) (hereinafter, may be referred to as "MSC group");
  (3) Human MSC ($1\times10^6$ cells) cultured under the stimulation with IFN-γ (hereinafter, may be referred to as "γ-MSC group");
  (4) Exosomes (2 μg) recovered from a normally cultured human MSC (hereinafter, may be referred to as "sEVs2 group");
  (5) Exosomes (2 μg) recovered from a human MSC cultured under the stimulation with IFN-γ (hereinafter, may be referred to as "γ-sEVs2 group");

(6) Exosomes (5 μg) recovered from a normally cultured human MSC (hereinafter, may be referred to as "sEVs5 group");
(7) Exosomes (5 μg) recovered from a human MSC cultured under the stimulation with IFN-γ (hereinafter, may be referred to as "γ-sEVs5 group")

Blood was collected from the reared mouse, serum was recovered, and the measurement of the amount of alanine aminotransferase (ALT), the measurement of the amount of alkaline phosphatase (ALP), and the measurement of the amount of albumin (ALB) in the serum were entrusted to Oriental Yeast Co., Ltd. Here, ALT is a hepatocyte damage marker. The results are shown in FIG. 11B.

Figure 11B:
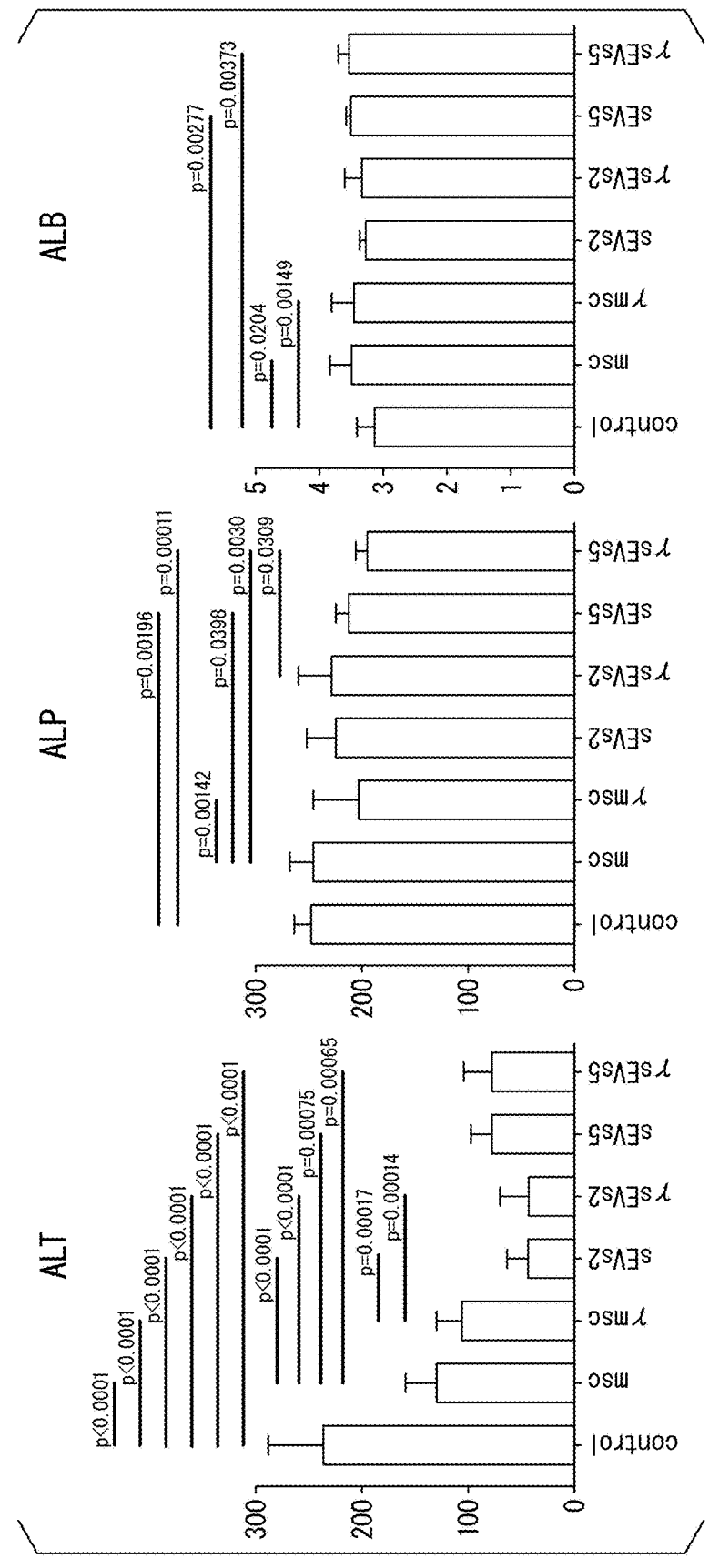
FIG. 11B is a graph showing the content of each component in serum collected from each mouse group in Example 7.

From FIG. 11B, there were no significant differences in the amounts of ALP and Alb between the groups; however, it can be seen that the ALB amount was slightly increased in the mouse group to which exosomes recovered from human MSC cultured under the stimulation with IFN-γ had been administered. The value of ALT, which is a hepatocyte damage marker, was remarkably decreased in the mouse group to which exosomes recovered from human MSC cultured under the stimulation with IFN-γ had been administered as compared with other mouse groups.

Figure 11C:
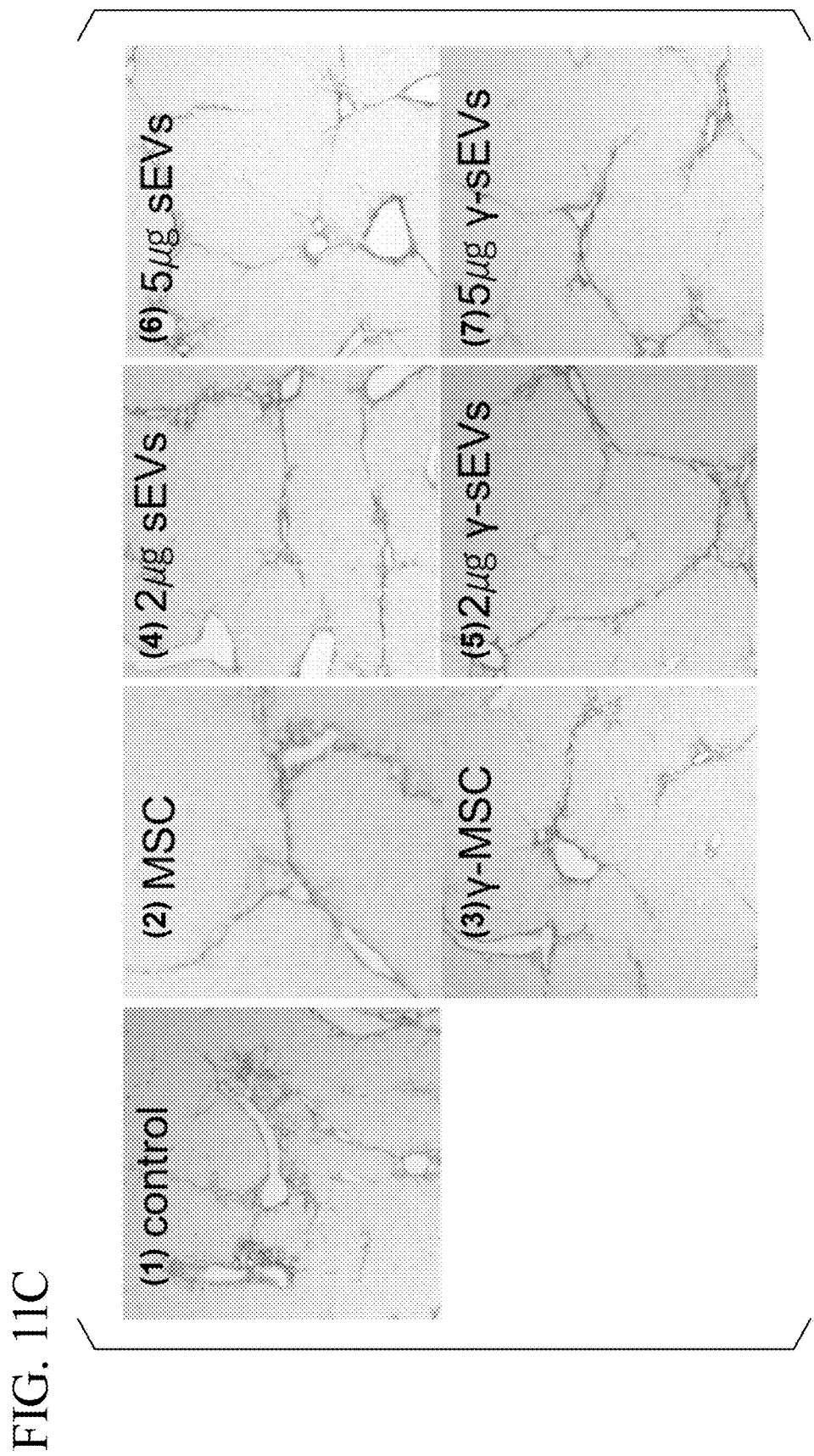
FIG. 11C is sirius red-stained images of liver slices respectively excised from mouse groups in Example 7.

In addition, the reared mouse was euthanized and the liver was excised. Liver slices were prepared and stained with sirius red to observe fibrosis. The results are shown in FIG. 11C. In FIG. 11C, (1) to (7) correspond to the mouse groups to which the above (1) to (7) had been administered, respectively. The same applies hereinafter. In addition, FIG. 11D is a graph showing the proportion of the stained area with respect to the total area of the stained image in the sirius red-stained image of the liver slice excised from each mouse group.

Figure 11D:
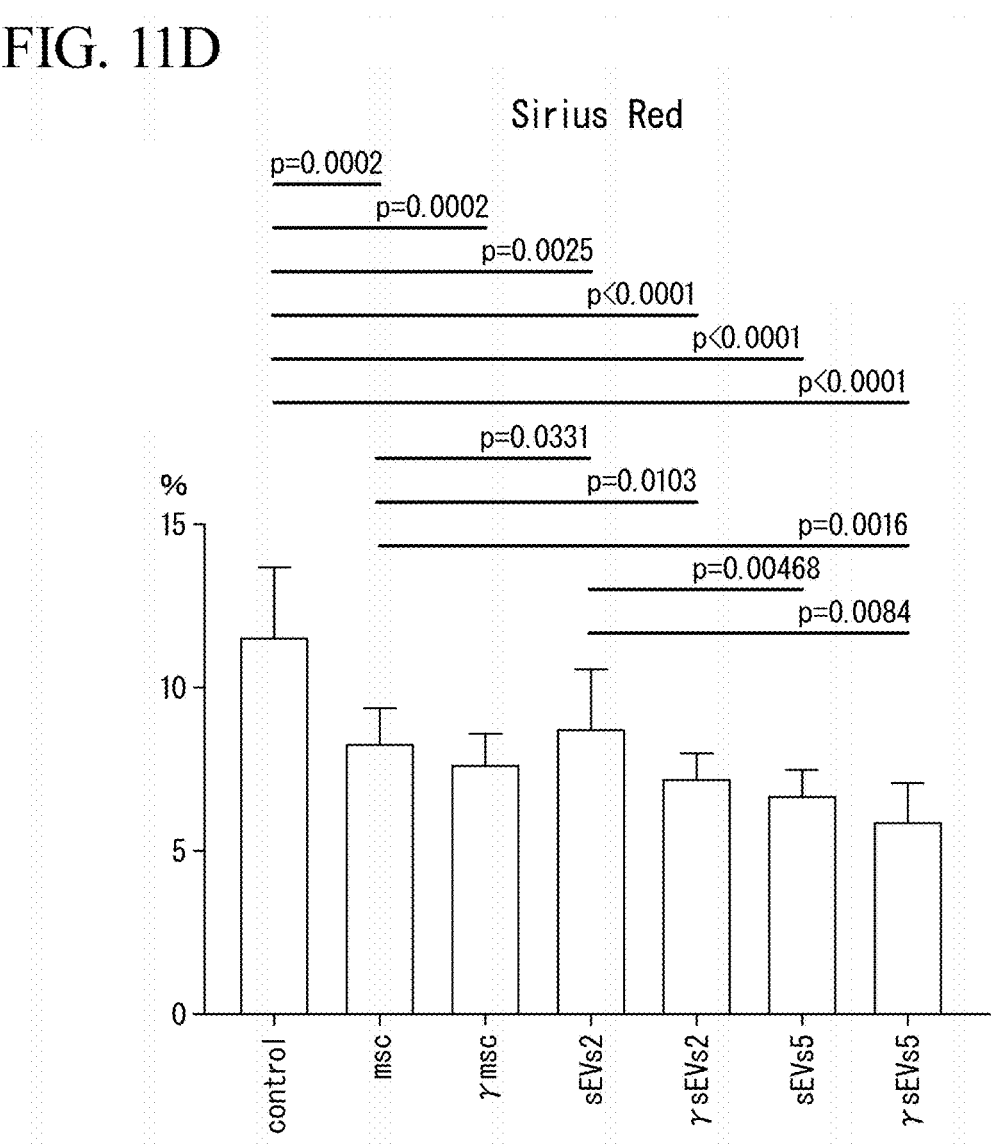
FIG. 11D is a graph showing the proportion of the stained area with respect to the total area of the stained image in the sirius red-stained image of the liver slice excised from each mouse group in Example 7.

From FIG. 11C and FIG. 11D, the proportion of the fibrotic tissue was decreased in the mouse group to which exosomes recovered from human MSC cultured under the stimulation with IFN-γ had been administered as compared with other mouse groups. In addition, the proportion of the fibrotic tissue tended to be decreased depending on the dose of exosomes recovered from human MSC cultured under the stimulation with IFN-γ.

Further, using the liver tissue excised from the reared mouse, the amount of hydroxyproline (Hydroxyproline) was measured using the QuickZyme Hydroxyproline Kit (QZB-HYPRO1). Here, hydroxyproline is a fibrosis marker. The results are shown in FIG. 11E.

Figure 11E:
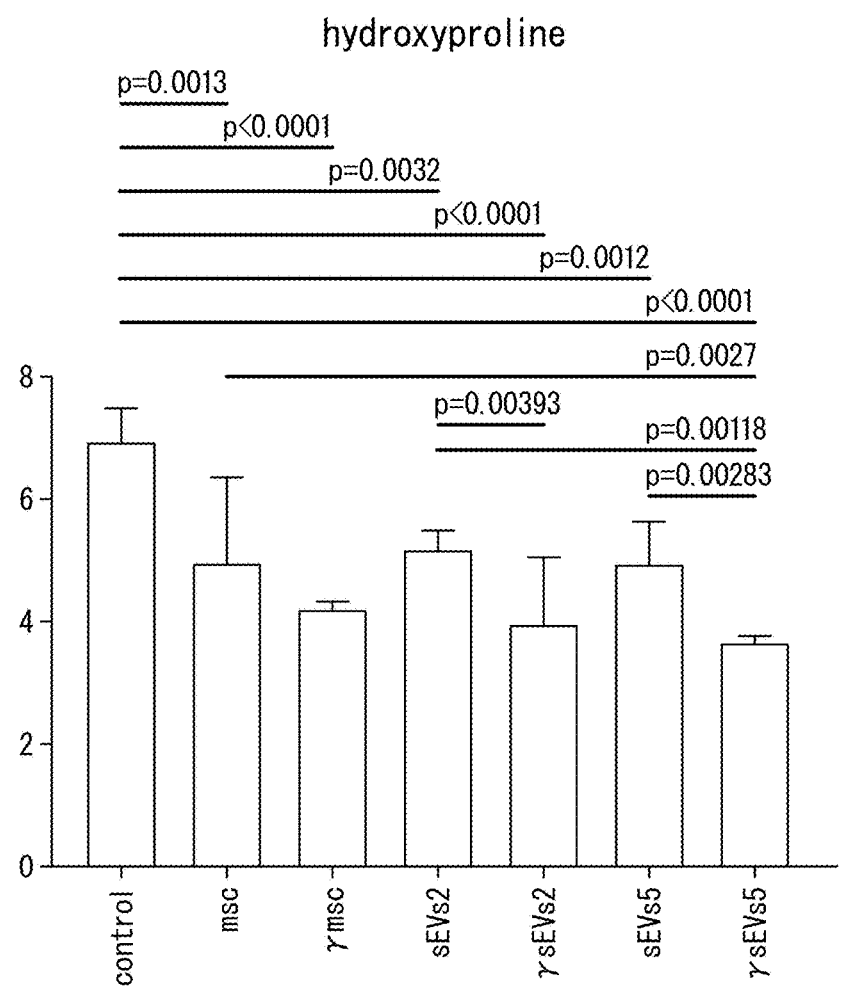
FIG. 11E is a graph showing the content of hydroxyproline in liver tissue collected from each mouse group in Example 7.

From FIG. 11E, it can be seen that the amount of hydroxyproline, which is a fibrosis marker, also tends to be decreased in the mouse group administered with exosomes recovered from human MSC cultured under the stimulation with IFN-γ as compared with other mouse groups.

From the above, it was suggested that liver damage can be ameliorated by administering exosomes recovered from human MSC cultured under the stimulation with IFN-γ.

Example 8

(Single Cell RNA-Seq Analysis)

Single cell RNA-seq analysis is a method of analyzing the gene expression of one single cell using a next-generation sequencer. Using the single cell RNA-seq analysis, changes in the behavior of various immune-related cells due to the administration of exosomes to a liver damage model mouse were investigated.

1. Exosome Administration to Liver Damage Model Mouse

Carbon tetrachloride was intraperitoneally administered to a wild-type mouse (C57BL/6J) for 8 weeks to prepare a liver damage model mouse. Next, any one of the following (1) to (5) was administered to the tail vein at the 8th week (on the 56th day), and the mouse was further reared for 4 weeks.

(1) PBS (Control group);
(2) Normally cultured human MSC ($1 \times 10^6$ cells);
(3) Human MSC ($1 \times 10^6$ cells) cultured under the stimulation with IFN-γ;
(4) Exosomes (2 kg) recovered from a normally cultured human MSC;
(5) Exosomes (2 g) recovered from a human MSC cultured under the stimulation with IFN-γ;

2. Single Cell RNA-Seq Analysis

The liver was excised from the reared mouse. The excised liver tissue was made into a single cell population using a liver dissociation kit (manufactured by Miltenyi Biotec). Next, flow cytometry was performed focusing on the fraction containing blood cells in the single cell population, and after sorting, each cell was analyzed. Then, the cells were captured on a 10× Genomics Chromium controller and prepared as a sequencing library according to the Chromium Single Cell 3' Reagent Kits V2 User Guide (10× Genomics PN-120237). The prepared library was sequenced using Illumina HiSeq 2500 and analyzed using a 10× cell ranger pipeline (ver. 3.0.2) and Seurat (ver 3.0). The clustering results visualized by t-distributed stochastic neighbor embedding (t-SNE) are shown in FIG. 12A.

Figure 12A:
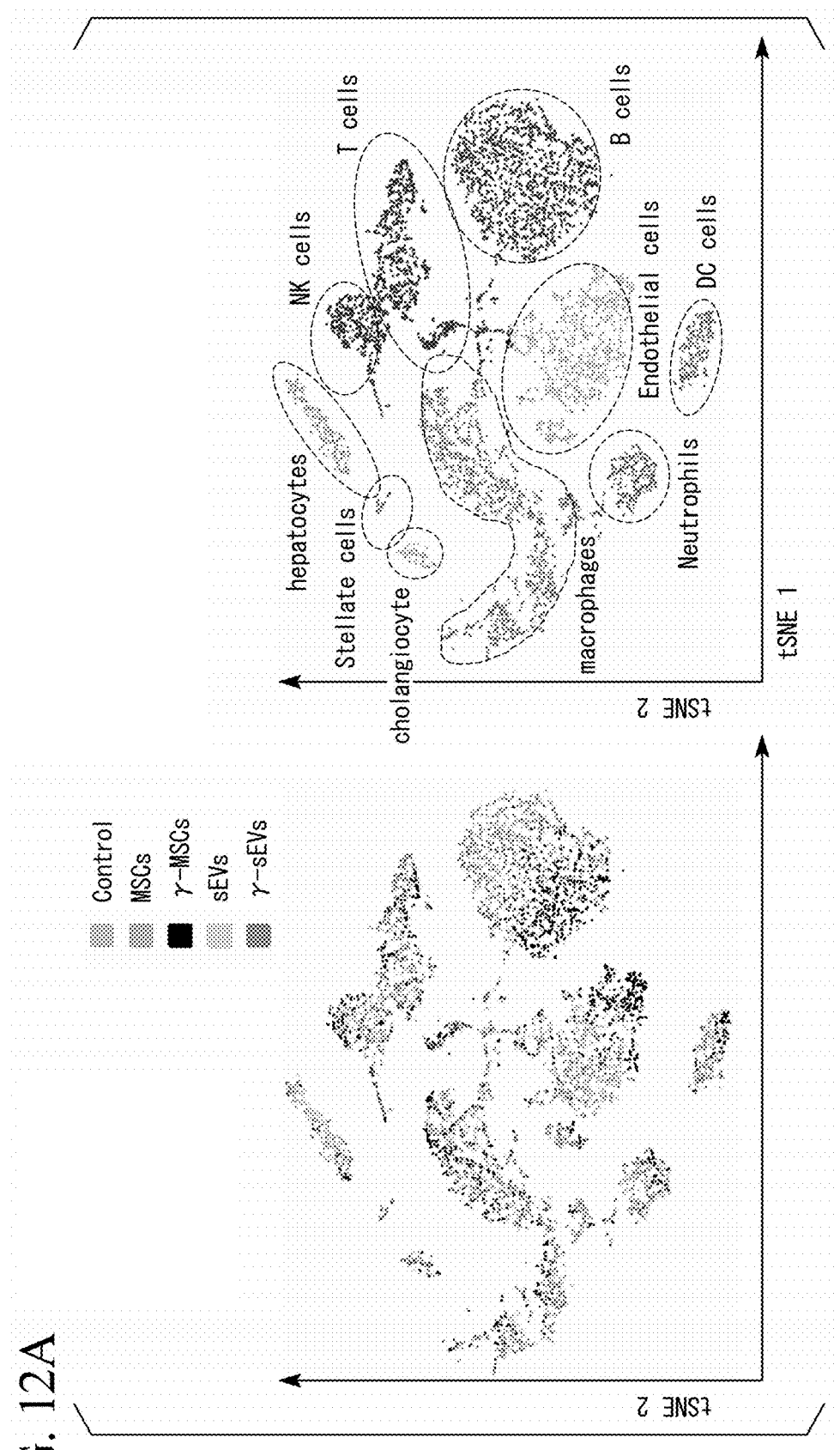
FIG. 12A is images showing clustering results visualized by t-distributed stochastic neighbor embedding (t-SNE) in a single cell RNA seq analysis using liver tissue collected from each mouse group in Example 8. The image on the left is shown for each mouse group, and the image on the right is shown for each cluster.
Figure 12B:
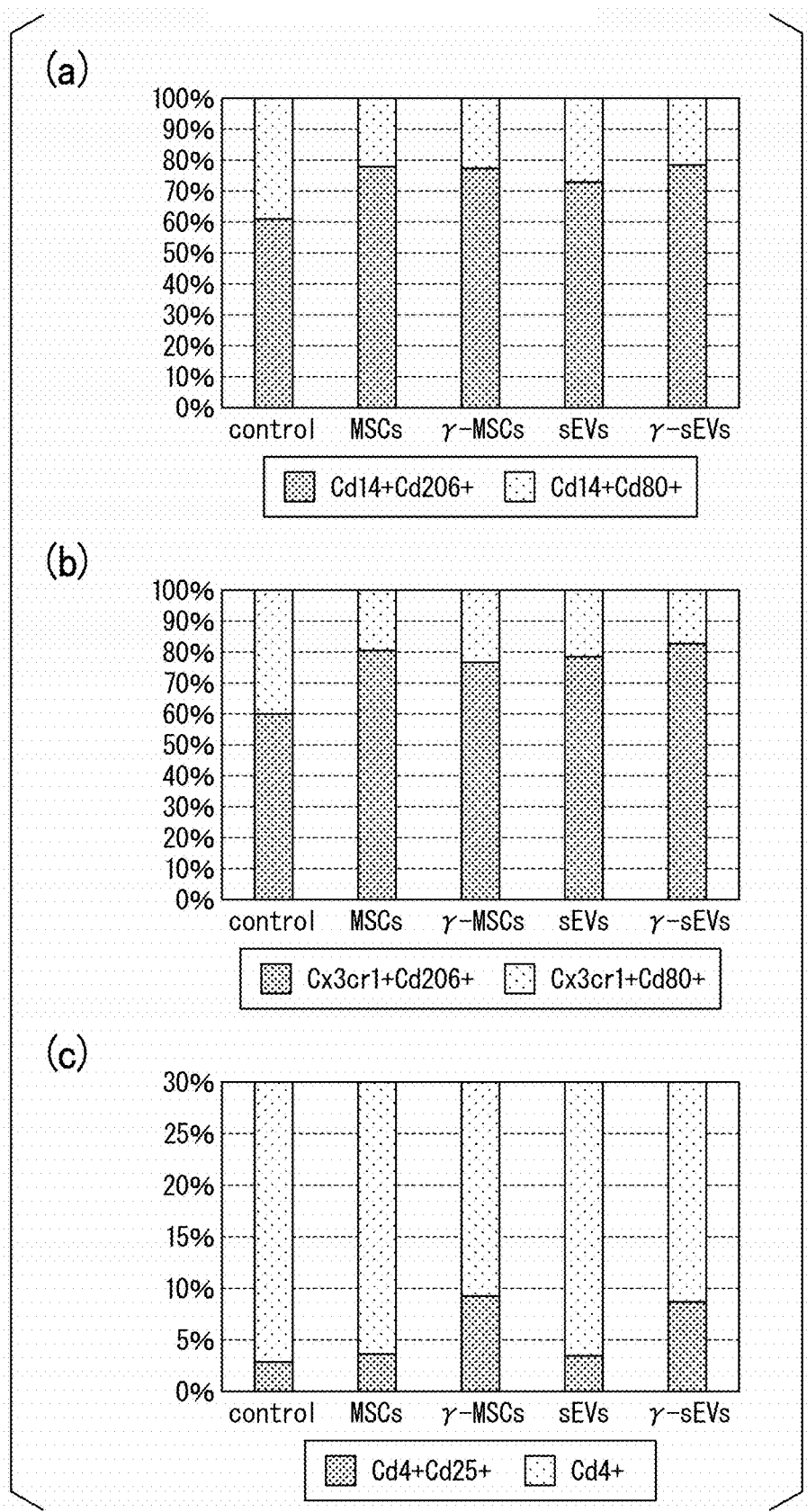
FIG. 12B is graphs showing the composition ratio between two types of cells identified with marker genes in each mouse group in the single cell RNA seq analysis using the liver tissue collected from each mouse group in Example 8.

In FIG. 12A, the image on the left is an image for each mouse group, and the image on the right is an image for each cluster (after estimating the cell type). In addition, FIG. 12B is graphs showing the composition ratio between the two types of cells identified with marker genes in each mouse group. In FIG. 12B, "Cd14+; Cd206+" in (a) is an M2 macrophage, and "Cd14+; Cd80+" is an M1 macrophage. "Cx3cr1+; Cd206+" in (b) is an M2 macrophage, and "Cx3cr1+; Cd80+" is an M1 macrophage. "Cd4+; Cd25+" in (c) is a regulatory T cell, and "Cd4+" is all cells that are Cd4-positive (expressing Cd4).

From FIG. 12A and FIG. 12B, in the mouse group administered with exosomes recovered from human MSC cultured under the stimulation with IFN-γ, it can be seen that the polarity of the macrophage was changed, the proportion of the macrophages induced into M2 macrophages was increased, and further, the proportion of regulatory T cells was increased, as compared with other mouse groups.

INDUSTRIAL APPLICABILITY

According to the induction method for a macrophage and the anti-inflammatory macrophage-inducing agent according to the present embodiments, it is possible to obtain an anti-inflammatory macrophage. According to the pharmaceutical composition of the present embodiment, which contains the inducing agent, it is possible to treat or prevent a disease associated with inflammation or fibrosis.

What is claimed is:

1. An anti-inflammatory macrophage-inducing agent, comprising exosomes produced from a mesenchymal stem cell to which interferon gamma has been added,
    wherein the exosomes comprise at least one protein selected from the group consisting of Annexin A1, Lactotransferrin, and Aminopeptidase N, as an active component.

2. A pharmaceutical composition, comprising the inducing agent according to claim 1.

3. The pharmaceutical composition according to claim 2, wherein the pharmaceutical composition is for anti-inflammatory use.

4. The pharmaceutical composition according to claim 2, wherein the pharmaceutical composition is for anti-fibrotic use.

5. The pharmaceutical composition according to claim 2, wherein the pharmaceutical composition is used for treating hepatitis or liver cirrhosis.

6. A method of treating fibrosis in a subject in need thereof, by administering to the subject a therapeutically effective amount of the agent of claim 2.

7. A method of increasing the level of regulatory T cells in a subject in need thereof, by administering to the subject a therapeutically effective amount of the agent of claim 2.

8. A method of inducing a macrophage to have anti-inflammatory activity, by contacting the macrophage with a therapeutically effective amount of the composition of claim 2.

* * * * *